United States Patent
Zagury et al.

(10) Patent No.: US 7,887,811 B2
(45) Date of Patent: Feb. 15, 2011

(54) METHOD FOR PREPARING A STABLE IMMUNOGENIC PRODUCT COMPRISING ANTIGENIC HETEROCOMPLEXES OF TNFα AND A CARRIER PROTEIN

(75) Inventors: Daniel Zagury, Paris (FR); Hélène Le Buanec, Paris (FR)

(73) Assignee: Neovacs, Paris (FR)

( * ) Notice: Subject to any disclaimer, the term of this patent is extended or adjusted under 35 U.S.C. 154(b) by 13 days.

(21) Appl. No.: 11/915,044

(22) PCT Filed: May 24, 2006

(86) PCT No.: PCT/EP2006/005044
§ 371 (c)(1),
(2), (4) Date: Nov. 20, 2007

(87) PCT Pub. No.: WO2007/022813
PCT Pub. Date: Mar. 1, 2007

(65) Prior Publication Data
US 2008/0193473 A1    Aug. 14, 2008

(30) Foreign Application Priority Data
May 24, 2005 (EP) .................................. 05300404

(51) Int. Cl.
*A61K 39/385* (2006.01)
(52) U.S. Cl. .............. 424/194.1; 424/195.11; 424/198.1
(58) Field of Classification Search ........................ None
See application file for complete search history.

(56) References Cited

U.S. PATENT DOCUMENTS 5,223,395 A * 6/1993 Gero ........................ 435/7.1
5,578,308 A * 11/1996 Capiau et al. ............ 424/240.1
2004/0028647 A1    2/2004 Zagury et al.
2004/0185058 A1    9/2004 Zagury et al.
2006/0067944 A1 * 3/2006 Le Buannec et al. ..... 424/187.1

FOREIGN PATENT DOCUMENTS

| EP | 1243256 | 9/2002 |
|---|---|---|
| WO | WO 91/01146 | 2/1991 |
| WO | WO 95/05849 | 3/1995 |
| WO | WO 2004/024189 | 3/2004 |
| WO | WO 2004024189 A1 * | 3/2004 |

OTHER PUBLICATIONS

Cheng et al.,, J Biol Chem. Jun. 10, 1979;254(11):4698-706.*
Tamura et al., J Biol Chem. Jan. 25, 1976;251(2):414-23.*
Yamamoto et al., Nat Biotechnol. May 2003;21(5):546-52.*
Del Giudice et al., Molecular Aspects of Medicine, vol. 19, Issue 1, Feb. 1998, pp. 1-70.*
Nencioni et al., Infect Immun. Feb. 1991;59(2):625-30.*
Ou et al., Eur J Biochem. Nov. 2001;268(22):5901-11.*
Liddel JE: "Immunization of Mice for Monoclonal Antibody Production" [Online] 2002, Macmillan Publisher, Nature Publishing Group.
Waterston A.M. et al.: Phase I Study of TNF-alpha Autovaccine in Patients with Metastatic Cancer Cancer Immunol Immunother vol. 54, Mar. 8, 2005, pp. 848-857.
Doolin EE et al.: "Mucosal *immunity* in the brushtail possum (*Tricosurus vulpecula*): Detection of Antibody in serum at female reproductive sites after intranasal immunization" Immunology and Cell Biology. vol. 80. 2002, pp. 358-363.
Bizzini B and Achour A: "Kinoids: the Basis for Anticytokine Immunization and their Use in HIV Infection" Cellular and Molecular Biology, vol. 41, Feb. 7, 1995, pp. 351-356.

* cited by examiner

*Primary Examiner*—Zachary Skelding
(74) *Attorney, Agent, or Firm*—Young & Thompson

(57) ABSTRACT

The present invention concerns a novel method for preparing a stable immunogenic product comprising antigenic heterocomplexes of TNFα and a carrier protein, the method steps of which are disclosed in the specification.

16 Claims, 11 Drawing Sheets

US 7,887,811 B2

Figure 1:
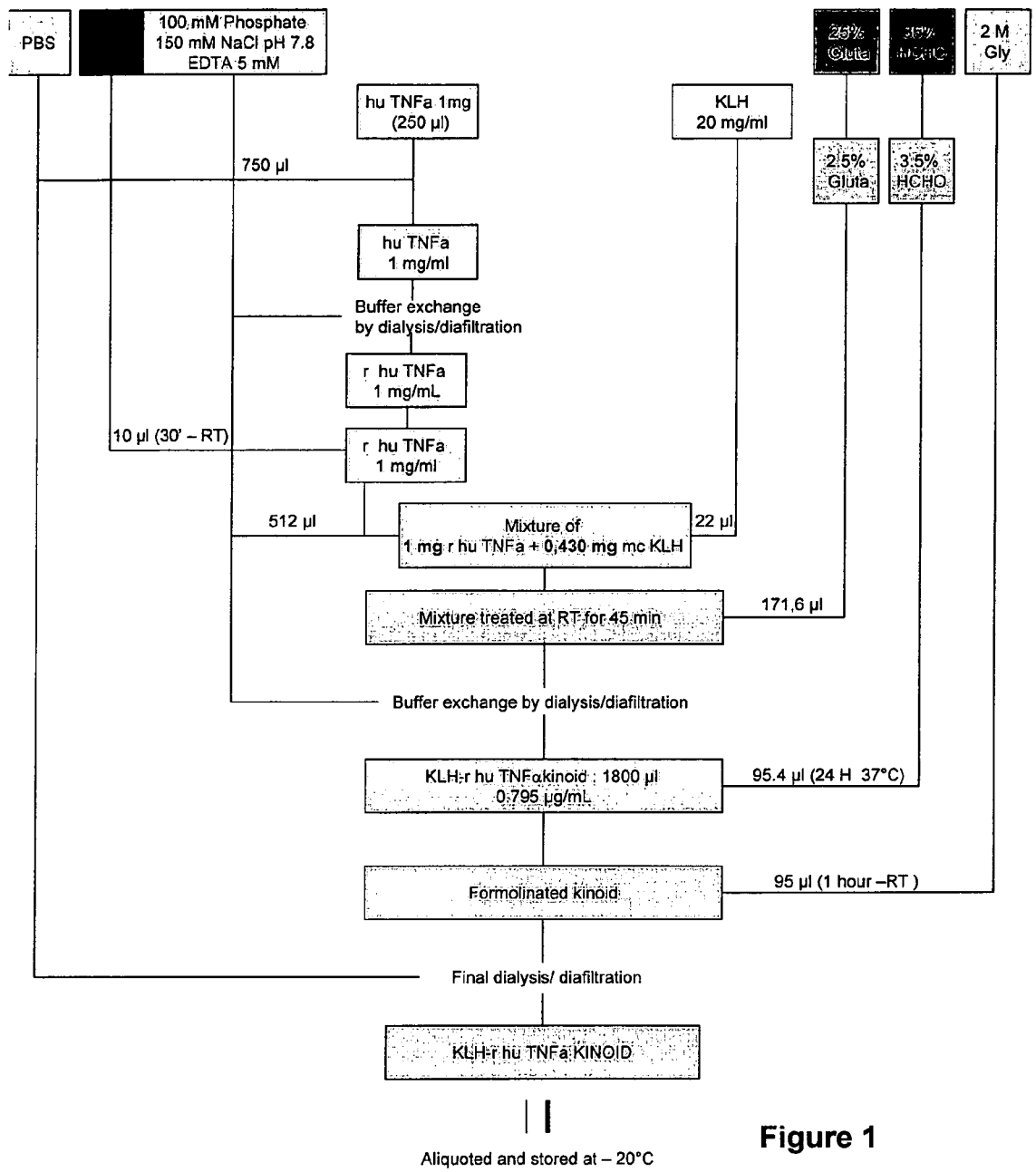

METHOD FOR PREPARING A STABLE IMMUNOGENIC PRODUCT COMPRISING ANTIGENIC HETEROCOMPLEXES OF TNFα AND A CARRIER PROTEIN

FIELD OF THE INVENTION

The present invention relates to stable immunogenic product comprising antigenic heterocomplexes of TNFα and a carrier protein for obtaining a humoral immune response in a mammal with production of antibodies that neutralize the biological activity of TNFα, as well as to a method for preparing the same.

The said stable immunogenic product may also be termed an anti-TNFα immunogenic product or also an immunogenic product for inducing anti-TNFα antibodies.

This invention further relates to vaccine compositions comprising said stable immunogenic product comprising antigenic heterocomplexes of TNFα and a carrier protein as well as to methods for preparing the same.

BACKGROUND OF THE INVENTION

A general method for preparing a stable immunogenic product comprising antigenic heterocomplexes comprising one or more antigenic proteins of interest and at least one carrier protein has been described in the PCT application published under n° WO 2004/024189 in the name of NEOVACS. Notably, said PCT application disclosed a method for preparing such heterocomplexes using TNFα as the antigen of interest and KLH as the carrier protein. Said general prior art method, when carried out for preparing heterocomplexes comprising TNFα and KLH, comprised the following steps:
  a) obtaining a mixture of KLH with TNFα;
  b) adding to said mixture glutaraldehyde at a final concentration of 0.026 M;
  c) removing excess glutaraldehyde by performing a dialysis;
  d) adding formaldehyde to the dialyzed solution and maintaining the presence of formaldehyde during a period of time of 48 hours;
  e) adding glycine to the solution obtained at the end of step d); and
  f) performing a dialysis with the solution obtained at the end of step e).

The examples of the PCT application n° WO 2004/024189 showed that the resulting TNFα/KLH immunogenic product was stable and able to raise the production of antibodies which possess a good neutralizing activity against native TNFα.

However, with time, it appeared that more efficient heterocomplexes were needed in view of satisfying the high level of requirements from the various Health authorities, including in the United States and in Europe, for the purpose of manufacturing suitable vaccine compositions containing said heterocomplexes as the main active ingredient.

DETAILED DESCRIPTION OF THE INVENTION

The applicant has found that the general method disclosed in the PCT application n° WO 2004/024189, when applied to heterocomplexes comprising TNFα and a carrier protein, led to final immunogenic products wherein both inactivation and immunogenicity of TNFα had to be improved, with the view of manufacturing anti-TNFα vaccine compositions to be approved by the various Health authorities throughout the world. The applicant has also found that stability of the whole immunogenic product should be improved, notably for increasing its stability with the time of storage.

The applicant has now found a novel method for preparing a stable immunogenic product comprising antigenic heterocomplexes of TNFα and a carrier protein that allows reaching the various goals described above.

An object of the present invention consists of a method for preparing a stable immunogenic product comprising antigenic heterocomplexes of TNFα and a carrier protein, comprising the steps of:
  a) providing a liquid solution containing TNFα;
  b) adding EDTA to said liquid solution containing TNFα of step a);
  c) adding a carrier protein to the liquid solution obtained at the end of step b), so as to obtain a liquid mixture of TNFα and said carrier protein;
  d) adding glutaraldehyde to the liquid mixture obtained at the end of step c), so as to partially covalently conjugate TNFα molecules to said carrier protein and obtain heterocomplexes between TNFα and said carrier protein;
  e) removing glutaraldehyde and free molecules of both TNFα and said carrier protein from the solution obtained at the end of step d), so as to obtain a liquid solution containing purified heterocomplexes between TNFα and said carrier protein;
  f) adding formaldehyde to the liquid solution obtained at the end of step e), and maintaining the presence of formaldehyde for a period of time ranging from 96 hours to 192 hours;
  g) adding a reagent blocking the reaction with formaldehyde to the liquid solution containing heterocomplexes between TNFα and said carrier protein, obtained at the end of step f); and
  h) removing formaldehyde and the blocking reagent from the liquid solution obtained at the end of step h), so as to obtain a liquid solution containing said stable immunogenic product comprising heterocomplexes between TNFα and said carrier protein;

By performing the method described above, the resulting stable immunogenic products are endowed with increased ability to induce the production of antibodies that neutralize native TNFα, when administered to a mammal in combination with one or more immunoadjuvant compounds.

A "stable immunogenic product comprising antigenic heterocomplexes of TNFα and a carrier protein", as used herein, consists of an immunogenic product that induces antibodies that neutralize the biological activity of TNFα, which immunogenic product comprises protein associations between (i) TNFα molecules and (ii) carrier molecules, wherein less than 40% of the TNFα molecules are bound to the carrier molecules by covalent chemical bonds.

The stable immunogenic product prepared by the method above is "immunogenic" because it induces antibodies against native TNFα in a subject, after its administration to the said subject, and more specifically antibodies that neutralize the biological activity of the native TNFα.

The immunogenic product prepared by the method above is "stable", since the said immunogenic product possesses its own isoelectric point that can be distinguished from the isoelectric point of at least (i) TNFα or (ii) the carrier molecule, and since the said immunogenic product migrates, in an isoelectrofocusing assay, as a protein band that is distinct from at least one of the two protein bands corresponding to (i) TNFα and (ii) the carrier molecule, respectively. This means that an immunogenic product according to the invention does not comprise free unbound TNFα molecules nor free unbound carrier protein molecules.

The immunogenic product prepared by the method above comprises "antigenic heterocomplexes" or "heterocomplexes" of TNFα and a carrier protein because the said immunogenic product comprises (i) the antigenic TNFα and (ii) the antigenic carrier protein molecules that are bound together (a) partially by covalent bonds (less than 40% covalent bonds) and (b) partially by weak non-covalent bonds (more than 60% non-covalent bonds), encompassing ionic interactions, hydrogen bonds, Van der Waals interactions, etc.

The stable immunogenic product comprising antigenic heterocomplexes of TNFα and a carrier protein that is defined above, that can be prepared according to the method of the invention, may also be more simply termed herein as an immunogenic product for inducing, or which induces, anti-TNFα antibodies in a human or an animal, or also as an anti-TNFα immunogenic product.

Thanks to the combined steps of the method according to the invention, the final stable immunogenic product is obtained with a higher reproducibility than the heterocomplexes comprising TNFα and a carrier protein obtained according to the prior art method disclosed in the PCT application no WO 2004/024189 cited above.

Notably, it has been found that the immunogenic activity of the stable immunogenic products prepared by performing the method according to the invention was very reproducible, from one preparation batch to another.

As shown in the examples herein, the stable immunogenic products prepared by performing the method according to the invention are devoid of detectable TNFα biological activity, both in vitro and in vivo, since the $ED_{50}$ dose is greater than 50 ng/ml, and even greater than 400 ng/ml, as expressed as final TNFα concentration.

Also, it is shown herein that beyond the induction of high anti-TNFα antibody titers, the stable immunogenic products prepared by performing the method according to the invention induce the production of highly neutralizing anti-TNFα antibodies having a neutralizing capacity $NC_{50}$ of beyond $\frac{1}{1000}$.

Further, it has also been shown that the stable immunogenic products prepared by performing the method according to the invention can be safely administered to mammals, since these products do not induce any adverse side effect, and particularly no inflammation nor any alteration of the organs such as heart, lungs, liver and spleen even when administered in an amount of 4000 times the Single Human Therapeutic Dose (SHTD).

Additionally, the stable immunogenic products prepared by performing the method according to the invention induce a strong production of anti-TNFα neutralizing antibodies, specifically of the IgG isotype, in Rhesus macaques, which shows that these stable immunogenic products are able to break immunological tolerance for endogenously produced proteins and induce an effective vaccination leading to neutralization of TNFα, which vaccination is able to prevent deleterious effects of over-production of TNFα in all pathological situations wherein TNFα is involved It has been further shown that the stable immunogenic products prepared by performing the method according to the invention are able to effectively vaccinate mammals against TNFα-induced arthritis. Still further, it has been shown that these stable immunogenic products are able to prevent and/or treat TNFα-induced arthritis inflammatory synovitis and articular destruction when used alone, with no need to complement the preventive or curative treatment with any additional anti-arthritis active ingredient, like methotrexate.

It has also been shown that the stable immunogenic products prepared according to the method of the invention were able to prevent and/or treat lethal shock caused by overproduction of TNFα.

Thus, the stable immunogenic products prepared according to the present invention induce an anti-TNFα autoimmune protection against acute and chromic TNFα dependent pathologies, without detectable side effects.

Without wishing to be bound by any particular theory, the applicant believes that the specific combination of steps a) to h) allows preserving the spatial conformation of the TNFα starting product while enhancing exposure of the major antigenic epitopes of TNFα to the solvent, so as to maximize an efficient presentation of the TNFα antigen to the immunocompetent cells, when the stable immunogenic product is administered to a mammal.

Without wishing to be bound by any particular theory, the applicant also believes that the specific combination of steps a) to h) allows both a better structural and chemical stabilization of the final immunogenic product, when TNFα and KLH are used, than the method disclosed in the PCT application n° WO 2004/024189. Such specific features of the resulting stable immunogenic products obtained by the method should allow the preparation of vaccine compositions that are also very stable during a long time period of storage.

Further, it has been found that the method of the invention allows the preparation of a final stable immunogenic product that is endowed with no residual biological activity of the TNFα starting product. Notably it has been found that the $ED_{50}$ of the TNFα starting product was of about 10 pg/mL of the invention. The final stable immunogenic product obtained by the method of the invention has an $ED_{50}$ value of more than 50 ng/mL, and even in most cases more than 400 ng/mL. In the same time, the final stable immunogenic product is endowed with a high immunogenicity.

Yet further, it has been shown that the immunogenic product obtained by the method according to the invention has preserved the main conformation of the native TNFα since the said immunogenic product still binds to TNFα receptors R1 and R2, despite its biological inactivation.

At step a), TNFα consists of a native TNFα selected from the group consisting of mouse TNFα, rat TNFα, rabbit TNFα and human TNFα. Preferably, TNFα consists of human TNFα.

In certain embodiments of the method according to the invention, step b) comprises the following steps:

b1) adding EDTA to said liquid solution containing TNFα of step a); and b2) adding DMSO to the liquid solution obtained at the end of step b1).

It has been found according to the invention that adding DMSO at step b2) enhanced the immunogenicity of the final stable immunogenic product.

In certain embodiments of the method, step d) comprises the following steps:

d1) adding glutaraldehyde to the liquid mixture obtained at the end of step c), so as to partially covalently conjugate TNFα molecules to said carrier protein and obtain heterocomplexes between TNFα and said carrier protein; and d2) adding EDTA to the heterocomplexes between TNFα and said carrier protein obtained at the end of step d1).

Thus, at the end of step d1), a liquid solution, containing a product which comprises TNFα molecules that are bound to the carrier molecules (i) partly by covalent bonds and (ii) partly by non-covalent bonds, is obtained.

The method according to the invention comprises step h) for removing formaldehyde and the blocking reagent from the solution obtained at the end of step g), so as to obtain a purified stable immunogenic product comprising heterocomplexes between TNFα and said carrier protein.

At the end of step h), the stable immunogenic product is obtained under the form of a translucent colorless liquid solution that is practically free of any visible particles.

In certain embodiments, said method may also comprise a further step i) of freezing the solution obtained at the end of step h).

In certain other embodiments, said method may also comprise a further step i) of lyophilizating the solution obtained at the end of step h), so as to obtain a white powder that can be stored for a long period of time before use.

In preferred embodiments of step a), TNFα concentration ranges from 0.1 mg/mL to 50 mg/mL, and even more preferably ranges from 0.5 mg/mL to 10 mg/mL.

In preferred embodiments of step b), final EDTA concentration ranges from 1 mM to 500 mM, and most preferably from 1 mM to 10 mM.

Advantageously, EDTA is added as a buffer solution having a pH ranging from 7 to 8.5, more preferably from 7.5 to 8.1.

In preferred embodiments of step b2), final DMSO concentration ranges from 0.5% v/v to 20% v/v, most preferably from 5% v/v to 20% v/v.

Advantageously, step b2) is carried out for a period of time ranging from 10 min to 50 min, more preferably from 20 min to 40 min.

In preferred embodiments of step c), the molar ratio of TNFα to said carrier protein ranges from 5:1 to 100:1, and even more preferably ranges from 20:1 to 80:1. In the most preferred embodiments of step c), the molar ratio of TNFα to said carrier protein ranges from 30:1 to 70:1, or from 40:1 to 60:1.

In preferred embodiments of step d), final glutaraldehyde concentration ranges from 0.05% w/w to 0.5% w/w. A glutaraldehyde final concentration ranging from 0.02 M to 0.03 M is suitable, with the most preferred final glutaraldehyde concentration consisting of 0.026 M.

Advantageously, step d2) is carried out for a period of time ranging from 30 min to 60 min, more preferably from 40 min to 50 min.

In preferred embodiments of step d2), final EDTA concentration ranges from 1 mM to 10 mM.

In preferred embodiments of step e), glutaraldehyde is removed by performing a dialysis, by performing an ultrafiltration with diafiltration or by performing Tangential Flow Filtration (TFF).

When dialysis is performed, a dialysis membrane with a cut-off threshold of 6-8 KDa is preferably used.

The dialysis step preferably comprises three steps, including (i) the two first steps performed with the working buffer (100 mM Phosphate, 150 mM NaCl pH 7.8, EDTA 5 mM) and (ii) the last step performed with PBS.

Usually, the dialysis step is performed with a conventional buffer solution, such as a Phosphate Buffer Saline solution (PBS), against 200 to 400 times the volume of the liquid solution containing the heterocomplexes between TNFα and the carrier protein, wherein the TNFα molecules are partly covalently conjugated to the carrier protein which is used.

When ultrafiltration with diafiltration is performed, a filtering membrane with a cut-off threshold of 10 000 KDa is preferably used, it being understood that the heterocomplexes between TNFα and the carrier protein are found in the ultrafiltration retentate. Usually, the liquid used for diafiltration consists of a buffer solution, such as a Phosphate Buffer Saline solution (PBS). Usually, the diafiltration is performed 3 times with an equal volume of buffer.

In preferred embodiments of step f), the final concentration of formaldehyde ranges from 1% w/w to 10% w/w, and even more preferably ranges from 2% w/w to 5% w/w.

At step f), the presence of formaldehyde is maintained during a period of time ranging from 96 hours to 192 hours.

It has been found according to the invention that maintaining the presence of formaldehyde with the heterocomplexes for a time period of less than 96 hours led to a final immunogenic compound that was significantly less stable with time, when compared with a stable immunogenic compound obtained according to the preferred embodiments of the method according to the invention.

On the other hand, it has been found according to the invention that maintaining the presence of formaldehyde with the heterocomplexes for a time period of more than 192 hours led to a final immunogenic compound that was highly stable but with a significantly lowered ability to induce antibodies having a high neutralizing activity against native TNFα.

More preferably, at step f), the presence of formaldehyde is maintained during a period of time ranging from 120 hours to 168 hours.

Most preferably, at step f), the presence of formaldehyde is maintained during a period of time ranging from 130 hours to 150 hours.

Advantageously, step f) is carried out at a temperature ranging from 30° C. to 42° C., more preferably from 35° C. to 39° C.

At step g) the reagent that blocks the reaction of the protein molecules with formaldehyde may consist of any suitable compound comprising at least one amino group and which will stop the chemical reaction of the protein molecules with formaldehyde.

In certain preferred embodiments, the said blocking reagent consists of glycine.

In preferred embodiments of step g), final glycine concentration ranges from 0.01 M to 10 M, and even more preferably ranges from 0.05 M to 2 M.

In certain other preferred embodiments of step g), the said blocking reagent consists of lysine.

In preferred embodiments of step g), final lysine concentration ranges from 0.01 M. to 10 M., preferably from 0.05 M to 2 M, and most preferably from 0.05 M. to 0.5 M.

In preferred embodiments, the protein molecules are brought into contact with lysine during an incubation time period from 1 hour to 10 days and most preferably from 5 days to 10 days.

A time period of incubation with lysine of more than 3 days, and most preferably of at least 5 days leads to an optimal irreversibility of the chemical structure of the final product and contributes to its good immunogenicity and stability.

Advantageously, when carrying out step h) the pH of the liquid solution is adjusted to a pH ranging from 6.8 to 7.8, more preferably from 7.0 to 7.6, for example by using a base such as NaOH.

In preferred embodiments of step h), formaldehyde and the blocking reagent are removed by performing a dialysis, by performing an ultrafiltration with diafiltration, or by performing Tangential Flow Filtration TFF).

The conditions for dialysis, ultrafiltration with diafiltration, or Tangential Flow Filtration (TFF) that are used in step h) are usually the same as those previously defined for step e) above, or as disclosed in the examples herein.

The terms "carrier protein" or "carrier protein molecule" are used herein according to their conventional meaning for the one skilled in the art, i.e. a protein which, when coupled to an antigenic molecule, including an hapten molecule, enables the induction of an immune response in a host organism against the said antigenic molecule, specifically in mammals including humans. As used herein, the said immune response encompasses production of antibodies directed against the said antigenic molecule.

According to the method of the invention, a wide diversity of carrier proteins known to the one skilled in the art may be used at step c). The carrier protein should bear sufficient helper T-cell epitopes so as to activate T-helper and B cells and induce these cells to release enough IL-1 and IL-2 to induce the expansion of the B cell clones that will produce the neutralizing anti-TNFα antibodies.

A <<carrier protein molecule>>, included in the stable immunogenic product of the invention, means any protein or peptide being at least 15 amino acids long, whatever its amino acid sequence, and which, when partially covalently being associated to the molecules of TNF α for forming protein heterocomplexes making up the immunogenic product of the invention, allows for a large number of molecules of TNFα to be presented to the B lymphocytes.

According to a first aspect, the carrier protein molecule consists of one protein or one peptide being at least 15 amino acid long, or also an oligomer of such a peptide, comprising one or more auxiliary T epitopes ("helper") able to activate auxiliary T lymphocytes ("T helper") of the host organism for producing cytokines, including interleukin 2, such cytokines, in turn, activating and inducing the proliferation of B lymphocytes, which, after maturation, will produce antibodies raised against TNFα.

The carrier protein molecule could also consist in a homo-oligomer or a homo-polymer of the native protein, from which it is derived, as well as a homo-oligomer or a homo-polymer of a peptide fragment of the native protein, from which it is derived. The antigenic protein of interest could also consist in a hetero-oligomer or a hetero-polymer comprising a combination of several distinct peptide fragments initially included in the native protein from which it is derived.

Examples of protein carriers which may be used when performing the method according to the invention include the Diphtheria and Tetanus toxoids (DT, DT CRM197, other DT mutants, e.g. position Glu-148, etc. [see, e.g., U.S. Pat. No. 4,709,017, WO93/25210, WO95/33481, etc.] and TT (and TT fragment C) respectively), Keyhole Limpet Haemocyanin (KLH), OMPC from *N. meningitides*, and the purified protein derivative of Tuberculin (PPD).

The function of the carrier is to provide cytokine help in order to enhance the immune response against TNFα. A non-exhaustive list of carriers which may be used in the present invention include: Keyhole limpet Haemocyanin (KLH), serum albumins such as bovine serum albumin (BSA), inactivated bacterial toxins such as tetanus or diphtheria toxins (TT and DT), or recombinant fragments thereof (for example, Domain 1 of Fragment C of TT, or the translocation domain of DT), or the purified protein derivative of tuberculin (PPD).

In an embodiment of the method, the carrier is Protein D from Haemophilus influenzae (EP 0 594 610 B1). Protein D is an IgD-binding protein from *Haemophilus influenzae* and has been patented by Forsgren (WO 91/18926, granted EP 0 594 610 B1). In some circumstances, for example in recombinant immunogen expression systems it may be desirable to use fragments of protein D, for example Protein D ⅓.sup.rd (comprising the N-terminal 100-110 amino acids of protein D (WO 99/10375; WO 00/50077)).

Thus, in preferred embodiments of the method, said carrier protein is selected form the group consisting of diphtheria toxoid (DT) and mutants thereof, Tetanus toxoid (TT), Keyhole Limpet Haemocyanin (KLH), and the purified protein derivative of Tuberculin (PPD), OMPC from *N. meningitidis*, the purified protein derivative of Tuberculin (PPD), bovine serumalbumin (BSA) and Protein D from *Haemophilus influenzae*.

Most preferably, said carrier protein consists of Keyhole Limpet Haemocyanin (KLH).

The present invention also relates to a method for preparing a vaccine composition comprising the steps of:
a) preparing a stable immunogenic product comprising antigenic heterocomplexes of TNFα by performing the method as defined above; and
b) combining said stable immunogenic product comprising antigenic heterocomplexes of TNFα prepared at step a) with one or more immunoadjuvants.

As shown in the examples herein, the stable immunogenic product, which may also be termed herein the anti-TNFα immunogenic product, which consists of the final product obtained by the method according to the invention, possesses specific physico-chemical and biological properties.

Generally, the anti-TNFα immunogenic product according to the invention possesses a molecular weight ranging from 50 kDa and 8000 kDa (8 MDa), with about 30% of the total protein amount having a molecular weight lower than 1000 kDa (1 MDa).

Further, the anti-TNFα immunogenic product according to the invention exhibits a molar ratio of TNFα to the said carrier protein ranging from 40:1 to 60:1.

Additionally, an anti-TNFα immunogenic product according to the invention, when incubated under denaturing conditions wherein non-covalent bonds are removed, like in an SDS-containing buffer, generate more than one protein products, which illustrates that the TNFα molecules and the carrier protein molecules comprised therein are, at least partly, bound together by non-covalent bounds, e.g. weak bonds encompassing ionic interactions, hydrogen bonds and Van der Waals bonds.

Further, it has been found that, in an anti-TNFα immunogenic product according to the invention, the covalent bonds between the TNFα molecules and the carrier protein molecules always represent less than 40% of the total bonds between these molecules, since always more than 60% of the TNFα molecules content of the said anti-TNFα immunogenic product are released as molecules unbound to the carrier protein under denaturing conditions.

As shown in the examples herein, including Example 8, an anti-TNFα immunogenic product according to the invention comprises at least the following protein species:
 TNFα molecules covalently bound to carrier protein molecules; and
 molecules that are bound by non-covalent bonds, including
  monomers of TNFα molecules;
  dimers of TNFα molecules;
  trimers of TNFα molecules;
  polymers of dimers and/or trimers of TNFα molecules;
  monomers of carrier protein molecules; and
  polymers of carrier protein molecules.

Importantly, the anti-TNFα immunogenic product according to the invention induces the production of anti-TNFα antibodies having a TNFα-neutralizing capacity ($NC_{50}$) beyond $1/1000$.

The TNFα-neutralizing capacity consists of the serum dilution that neutralizes 50% of the cytotoxic activity of TNFα. This biological feature of an anti-TNFα immunogenic product according to the invention is easily, directly and reliably assessed by the one skilled in the art using the conventional techniques that are disclosed in the examples and which are also detailed further in the present specification.

The $NC_{50}$ value of the anti-TNFα immunogenic product of the invention is clearly distinct from the $NC_{50}$ value found for the stable immunogenic product prepared according to the method disclosed in the prior PCT application n° WO 2004/024189.

Comparison between the $NC_{50}$ values of a specific anti-TNFα immunogenic product wherein the carrier protein consists of KLH is detailed in the examples herein, notably in Table 3.

The TNFα-KLH immunogenic product according to the invention consists of the batch referred to as "K7", whereas the corresponding stable immunogenic product prepared according to the method disclosed in the prior PCT application n° WO 2004/024189 consists of the batch referred to as "K10", as found in Table 3.

As shown in Table 3, the $NC_{50}$ value found for the stable immunogenic product prepared according to the method disclosed in the prior PCT application n° WO 2004/024189 is of 1/700. The $NC_{50}$ value found for the anti-TNFα immunogenic product according to the invention is 1/1200, thus approximately half the $NC_{50}$ value found for the prior art product.

This better TNFα neutralizing capacity of the anti-TNFα immunogenic product according to the invention is provided to the final product by the specific combination of features of the method according to the invention, including using of EDTA at step b), and maintaining the presence of formaldehyde for a period of time ranging from 96 hours to 192 hours at step f).

Particularly, as shown in Table 3 herein, maintaining the presence of formaldehyde for a period of time ranging from 96 hours to 192 hours at step f) is determinant for obtaining a final anti-TNFα immunogenic product endowed with the best low $NC_{50}$ values.

Further, as shown in Table 3 herein, maintaining the presence of formaldehyde for a period of time ranging from 96 hours to 192 hours at step f) allows also to obtain a final anti-TNFα immunogenic product wherein the TNFα cytotoxic activity has been almost completely blocked, with $ED_{50}$ (Effective Dose$_{50}$) values of more than 50 ng/ml, preferably of more than 400 ng/ml, and sometimes at least up to 10 pg/ml.

The assessment of the TNFα neutralizing capacity $NC_{50}$ value of an anti-TNFα immunogenic product according to the invention is disclosed in detail in Example 3 and is briefly detailed hereunder.

A typical method directly and reliably usable by the one skilled in the art for measuring the TNFα neutralizing capacity ($NC_{50}$) value of an anti-TNFα immunogenic product comprises the following steps:
  a) administering mice with a combination of the anti-TNFα immunogenic product to be tested and Complete Freund Adjuvant (CFA), via the intramuscular route;
  b) at Day 21 after step a), administering the same mice with a combination of the anti-TNFα immunogenic product to be tested in and Incomplete Freund Adjuvant (IFA), via the intramuscular route;
  c) At Day 28 after step a), collecting blood samples from each mouse treated at steps a) and b) above;
  d) determining which dilution of the sera originating from the blood samples collected at step c) inhibits 50% of the cytotoxic activity of a standard amount of TNFα.

For performing the $NC_{50}$ value assessment method above, TNFα cytotoxic activity is measured according to the conventional cytotoxicity test using the L929 cell line. Preferably, the standard amount of TNFα is of 20 ng/ml final concentration in the L929 cell cultures.

As disclosed in the examples herein, and specifically in Table 3 herein, the $ED_{50}$ value consist of the final concentration of an anti-TNFα immunogenic product according to the invention that induces 50% cytotoxicity in the conventional L929 cell cytotoxicity test.

It has been found that another feature that distinguishes an anti-TNFα immunogenic product according to the invention form the stable immunogenic product disclosed in the PCT application n° WO 2004/024189 consists of the $ED_{50}$, which is more than 50 ng/ml, and even more than 400 ng/ml, and sometimes up to 10 pg/ml, whereas an $ED_{50}$ of about 15 ng/ml was found for the prior art product.

Without wishing to be bound by any particular theory, the applicant believes that the better biological properties, including lack of TNF activity as well as high immunogenicity, of the anti-TNFα immunogenic product obtained by the method according to the invention illustrate that the anti-TNFα immunogenic product according to the invention is structurally distinct from the stable immunogenic products disclosed in the PCT Application N° WO2004/024189, although specific structural changes may be not easily detectable.

This invention also pertains to a stable immunogenic product comprising antigenic heterocomplexes of TNFα and a carrier protein which has one or more of the following technical features:
  (i) it comprises (1) TNF-α molecules and (2) carrier protein molecules that are bound together (a) by less than 40% covalent bonds and (b) by more than 60% non-covalent bonds;
  ii) it exhibits a molar ratio of TNFα to said carrier protein ranging from 40:1 to 60:1;
  iii) it induces the production of anti-TNFα antibodies having a TNFα neutralizing capacity ($NC_{50}$) of less than 1/1000; and
  iv) it possesses an $ED_{50}$ value of more than 50 ng/ml, and even more than 400 ng/ml, in the L929 cell cytotoxicity test.
  (v) it possesses a molecular weight ranging from 50 kDa to 8000 kDA (8 M Da), with about 30% of the total protein amount having a molecular weight lower than 1000 kDa (1 MDa).

Notably, the present invention relates to an anti-TNFα immunogenic product having the features (i) to (iv) above.

In certain embodiments, the carrier protein consists of KLH.

The percentage of carrier protein molecules and of TNFα proteins of interest linked between one another through covalent bonds in an immunogenic product of the invention can be easily checked by the man of the art.

For example, determining the percentage of TNFα molecules linked to the carrier protein molecules through a covalent link in an immunogenic product of the invention could be made using the following steps of:
  (i) submitting said immunogenic product in solution to denaturing and reducing conditions;
  (ii) performing a size exclusion chromatography step with the product as obtained at the end of step (ii) during which the various protein components with decreasing molecular mass are successively eluted from the size exclusion chromatography support;

(iii) measuring the amount of TNFα molecules linked through a covalent bond to the carrier molecule in the eluate fraction containing the protein components with the highest molecular mass;

(iv) comparing the amount of TNFα measured in step (iii) with the total amount of TNFα initially included in the starting immunogenic product.

In step (i) of the method for determining the above-described covalent link percentage, incubating a given amount (in number of moles or in weight) of the immunogenic product of the invention under denaturing and reducing conditions leads to a disassociation of the weak bonds between the various protein components not linked between one another through a covalent bond.

Amongst preferred denaturing conditions there is the presence of urea, for example, in the final 8M concentration, or the presence of SDS, for example, in the 1% final concentration in total weight of the solution containing the immunogenic product. Amongst preferred reducing conditions there is the presence of β-mercaptoethanol, for example in the 5% final concentration of the total volume of the solution containing the immunogenic product.

In step (ii) of the method for determining the percentage of molecules of TNFα and molecules of carrier protein linked between one another through covalent bonds, the size exclusion chromatography support is selected by the man of the art according to his technical general knowledge. For example, the man of the art could make use of chromatographic supports as marketed by the Pharmacia Corporation under the <<Superdex 75™, Superdex 200™ and Superdex 400™>>trade marks.

In step (ii), the molecular fraction corresponding to the carrier molecule covalently linked to the molecules of TNFα is eluted first, before the eluate fraction(s) containing the antigen of interest under a free form. The amount of TNFα being eluted under a free form corresponds to the fraction of the antigen of interest, which was not covalently linked to the carrier molecule, within the starting immunogenic product. It is on the high molecular mass protein fraction that occurs the measurement of the amount of TNFα covalently linked to the carrier protein molecule, for example, in an immuno-enzyme test, in a radioimmunologic test or in an immunofluorescence test, either direct or indirect (<<sandwich>>), using antibodies specific to TNFα and which do not have any immunologic reaction crossed with the carrier protein molecule.

In step (iii), the amount of TNFα covalently linked with the carrier protein molecule, being measured as described hereinabove, is 30 compared with the initial amount of TNFα being included in the given amount (in number of moles or in weight) of the starting immunogenic product and the percentage of TNFα is thereby calculated, which is covalently linked to the carrier protein molecule, in the immunogenic product of the invention.

The percentage of carrier protein molecules and of TNFα linked between one another through covalent bonds, in an immunogenic product of the invention, can be easily checked by the man of the art, making use of a second method comprising the following steps of:

a) immobilizing on a support of specifically antibodies raised against the carrier protein;

b) bringing into contact the antibodies raised against the carrier protein, which were immobilized on the support in step a), with a known amount of molecules of the immunogenic product to be tested comprising said carrier protein and TNFα;

c) removing the molecules of the immunogenic product which are not linked to the anti-carrier protein antibodies immobilized in step a), by means of a buffering aqueous solution comprising one ore more protein denaturing agents;

d) d1) bringing into contact (i) immunogenic complexes formed in step c) between the immobilized anti-carrier protein antibodies and the molecules of the immunogenic product with (ii) antibodies specifically raised against the carrier protein;

d2) separately from step d1), bringing into contact the immunogenic complexes formed in step c) between the immobilized anti-carrier protein antibodies and the molecules of the immunogenic product with (ii) antibodies specifically raised against TNFα;

e) e1) quantifying the antibodies added in step d1) having been linked to the carrier protein;

e2) quantifying the antibodies added in step d2) having been linked to TNFα;

f) calculating the ratio between:

(i) the amount of anti-carrier protein bound antibodies measured in step e1); and (ii) the amount of anti-TNFα bound antibodies measured in step e2), said ratio consisting in the proportion of carrier protein molecules and TNFα molecules being linked between one another through covalent bonds, within the starting immunogenic product.

In step c) of the above described method, the use of an aqueous washing solution containing one or more protein denaturing agents leads to a denaturation of the immunogenic product linked to the anti-carrier protein antibodies, resulting in the release, in the washing solution, of TNFα molecules which are not covalently linked to the carrier protein molecules. Therefore, in step d2) of the method, only the TNFα molecules being covalently linked to the carrier protein molecules are quantified.

Preferably, the denaturing buffering solution used in step c) contains a surfactant such as Tween®20, in a final concentration of 0.1% v/v.

in steps d1) and d2), the amounts of bound antibodies are preferably measured through incubating antigen-antibodies complexes formed at the end of each of said steps with a new antibody being labelled through a detectable molecule, respectively:

(i) in step d1), a new antibody directed against an the anti-carrier protein antibody and labelled with a detectable molecule;

(ii) in step d2), a new antibody directed against an antibody anti-TNFα and labelled with a detectable molecule.

The detectable molecule is indiscriminately either a radioactive molecule, a fluorescent molecule or an enzyme. As an enzyme, peroxydase could more particularly be used, its presence being revealed through colorimetry, after incubation with the ortho-phenylenediamine (OPD) substrate.

A detailed protocol of the above-mentioned method is described in the examples.

By way of illustration, it has been shown according to the invention, using the first or the second above described quantification methods that: in the immunogenic product comprising heterocomplexes between the KLH carrier molecule and human TNFα molecules, less than 40% of the TNFα molecules are covalently linked to the KLH carrier protein molecule.

To prepare an immunogenic or a vaccine composition of the invention, the stable immunogenic product obtained by the method according to the invention is adjusted to an appropriate concentration, optionally combined with a suitable vaccine adjuvant, and packaged for use.

This invention also pertains to an immunogenic composition comprising (i) a stable immunogenic product comprising antigenic heterocomplexes of TNFα and a carrier protein prepared by the method disclosed herein or (ii) a stable immunogenic product comprising antigenic heterocomplexes of TNFα and a carrier protein described above, in combination with one or more pharmaceutically acceptable excipients.

This invention also relates to a vaccine composition comprising (i) a stable immunogenic product comprising antigenic heterocomplexes of TNFα and a carrier protein prepared by the method disclosed herein or (ii) a stable immunogenic product comprising antigenic heterocomplexes of TNFα and a carrier protein described above, in combination with one or more immunoadjuvants.

As used herein, the term "adjuvant" refers to its ordinary meaning of any substance that enhances the immune response to an antigen with which it is mixed. Adjuvants useful in the present invention include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and *Corynebacterium parvum* are potentially useful adjuvants Any adjuvant known in the art may be used in the vaccine composition above, including oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), Biostim™ (e.g., 01K2), the "Iscoms" of EP 109 942, EP 180 564 and EP 231 039, aluminum hydroxide, saponin, DEAE-dextran, neutral oils (such as miglyol), vegetable oils (such as arachid oil), liposomes, Pluronic® polyols, the Ribi adjuvant system (see, for example GB-A-2 189 141), or interleukins, particularly those that stimulate cell mediated immunity. An alternative adjuvant consisting of extracts of *Amycolata*, a bacterial genus in the order Actinomycetales, has been described in U.S. Pat. No. 4,877,612. Additionally, proprietary adjuvant mixtures are commercially available. The adjuvant used will depend, in part, on the recipient organism. The amount of adjuvant to administer will depend on the type and size of animal. Optimal dosages may be readily determined by routine methods.

Suitable adjuvants include but are not limited to surfactants, e.g., hexadecylamine, octadecylamine, lysolecithin, dimethyidioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," Sem. Hematol., 30:3-15 (1993).

The adjuvant properties of saponin have been long known, as has its ability to increase antibody titers to immunogens. As used herein, the term "saponin" refers to a group of surface-active glycosides of plant origin composed of a hydrophilic region (usually several sugar chains) in association with a hydrophobic region of either steroid or triterpenoid structure. Although saponin is available from a number of diverse sources, saponins with useful adjuvant activity have been derived from the South American tree *Quillaja saponaria* (Molina). Saponin from this source was used to isolate a "homogeneous" fraction denoted "Quil A" (Dalsgaard, K., (1974), Arch. Gesamte Virusforsch. 44:243).

Dose-site reactivity is a major concern for both the veterinary and human use of Quil A in vaccine preparations. One way to avoid this toxicity of Quil A is the use of an immunostimulating complex (known as an ISCOM™, an abbreviation for Immuno Stimulating Complex). This is primarily because Quil A is less reactive when incorporated into immunostimulating complexes, because its association with cholesterol in the complex reduces its ability to bind to cholesterol in cell membranes and hence its cell lytic effects. In addition, a lesser amount of Quil A is required to generate a similar level of adjuvant effect.

The immunomodulatory properties of the Quil A saponins and the additional benefits to be derived from these saponins when they are incorporated into an immunostimulating complex have been described in various publications, e.g. Cox and Cox, J. C. and Coulter, A. R. Advances in Adjuvant Technology and Application in Animal Parasite Control Utilising Biotechnology, Chapter 4, Editor Yong, W. K. CRC Press (1992); Cox, J. C. and Coulter, A. R. (1997) Vaccine, 15(3):248-256; Cox, J. C. and Coulter, A. R. (1999) BioDrugs 12(6):439-453; Dalsgaard, (1974) (supra); Morein et al., (1989) "Immunostimulating complex (ISCOM)", In "Vaccines: Recent Trends and Progress". G. Gregoriadis, A. C. Allison and G. Poster (Eds). Plenium Press, New York, p. 153; Australian Patent Specifications Nos. 558258, 589915, 590904 and 632067.

Classic ISCOMs are formed by combination of cholesterol, saponin, phospholipid, and immunogens, such as viral envelope proteins. ISCOM matrix compositions (known as ISCOMATRIX™) are formed identically, but without viral proteins. ISCOMs appear to stimulate both humoral and cellular immune responses. ISCOMs have been made with proteins from various viruses, including HSV-1, CMV, EBV, hepatitis B virus (HBV), rabies virus, and influenza virus see for example, I. G. Barr et al., Adv. Drug Delivery Reviews, 32:247-271 (1998). It has been observed that where naked DNA or polypeptides from infectious agents are poorly immunogenic when given by themselves, inclusion within ISCOMs has increased their immunogenicity. Various proteins formulated with ISCOMs have been shown to induce CTL, mainly in rodent models. Berzofsky, (1991), Biotechnol. Ther. 2:123-135; Hsu et al., (1996), Vaccine 14:1159-1166; Lipford et al., (1994), Vaccine 12:73-80; Mowat et al., (1991), Immunology 72:317-322; Osterhaus et al., (1998), Dev. Biol. Stand. 92:49-58; Rimmelzwaan et al., (1997), J. Gen. Virol. 78 (pt. 4):757-765; Sambhara et al., (1998), J. Infect. Dis. 177:1266-1274; Sambhara et al., (1997), Mech. Aging Dev. 96:157-169; Sjolander et al., (1997), Vaccine 15:1030-1038; Sjolander et al., (1998), J. Leukoc. Biol. 64:713-723; Takahashi et al., (1990), Nature 344:873-875; Tarpey et al., (1996), Vaccine 14:230-236; Trudel et al., (1987), Vaccine 10:107-112; Verschoor et al., (1999), J. Virol. 73:3292-3300; Villacres-Eriksson, (1995), Clin. Exp. Immunol. 102:46-52; Zugel et al., (1995), Eur. J. Immunoll. 25:451-458.

Association between a stable immunogenic product obtained by the method of the invention and an adjuvant is thought to be important for optimal induction of immune responses. A number of studies have been done which confirm this hypothesis including work with virosomes and ISCOMs™ (Ennis, F. A., Crux, J., Jameson, J., Klein, M., Burt, D. and Thipphawong, J. 1999. Virology 259: 256-261., Zurbriggen, R., Novak-Hofer, I., Seelig, A. and Gluck, R. (2000), Progress in lipid Research 39: 3-18., Voeten, J. T. M., Nieuwkoop, N. J., Lovgren-Bengtsson, K., Osterhaus, D. M.

E. and Rimmelzwaan, G. F. 2000. Euro J Imm (Submitted)). Typically association between ISCOM™ and antigen has been achieved by incorporation of amphipathic antigens into the ISCOM™ structure during formation (Morein, B., B. Sundquist, S. Hoglund, K. Dalsgaard, and A. Osterhaus. 1984. Nature 308:457). Incorporation was by hydrophobic interactions. More recently methods to associate antigens with a preformed protein-free immunostimulating complex (ISCOMATRIX™) utilising chelating and electrostatic interactions have been deviated (International Patent Applications Nos. PCT/AU98/00080-WO 98/36772, and PCT/AU00/00110).

In certain embodiments of a vaccine composition according to the invention, said vaccine composition comprises, as pharmaceutical excipients, one or more charged inorganic carriers. Examples of charged organic carriers which are adjuvants suitable for use in the present invention include, but are not limited to, saponin, saponin complexes, any one or more components of the immunostimulating complex of saponin, cholesterol and lipid known as ISCOMATRIX™ (for example the saponin component and/or the phospholipid component), liposomes or oil-in-water emulsions. (The composition and preparation of ISCOMATRIX™ is described in detail in International Patent Application Number PCT/SE86/00480, Australian Patent Numbers 558258 and 632067 and European Patent Publication No. 0 180 564, the disclosures of which are incorporated herein by reference). Further examples of adjuvants include, but are not limited to, those detailed in the publications of Cox and Coulter, 1992, 1997 and 1999. It should be understood that the subject organic carrier may be naturally occurring or it may be synthetically or recombinantly derived.

The vaccine compositions may also include further adjuvants to enhance effectiveness of the composition. Suitable adjuvants include, but are not limited to: (1) aluminum salts (alum), such as aluminum hydroxide, aluminum phosphate, aluminum. sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles, (b) SAF, containing 10% Squalene, 0.4% Tween 80, 5% pluronic-blocked polymer, and thr-MDP (see below) either microfluidised into a submicron emulsion or vortexed to generate a large particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.); (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12, etc), interferons (e.g. gamma interferon), macrophage colony stimulating factor (M-CSF), etc.; (6) detoxified mutants of a bacterial ADP-ribosylating toxin such as a cholera toxin (CT), a pertussis toxin (PT), or an *E. coli* heat-labile toxin (LT), particularly LT-K63, LT-R72, CT-S109, PT-K9/G129; see, e.g. WO 93/13302 and WO 92/19265; (7) other substances that act as immunostimulating agents to enhance the effectiveness of the composition; and (8) microparticles with adsorbed macromolecules, as described in International Patent Application No. PCT/US99/17308. Alum and MF59 are preferred.

As mentioned above, suitable muramyl peptides include, but are not limited to, N-acetyl-muramyl-L-threonyl-D-isoglutamine (thr-MDP), N-acetyl-normauramyl-L-alanyl-D-isoglutamine (nor-MDP), N-acetylmuramyl-L-alanyl-D-isoglutaminyl-L-alanine-2-(1'-2'-dipalmitoyl-s-n-glycero-3-hydroxyphosphoryloxyethylamine (MTP-PE), etc.

Further adjuvants for inducing a mucosal or a systemic response against an immunogeinc compound according to the invention may be those that are described in the book of Vogel et al. (Vogel F. R., Powell M. F. and Alving C. R., <<A compendium of vaccine adjuvants and excipients>>; $2^{nd}$ Edition; Vogel F. R. and Powell M F, 1995, <<A summary compendium of vaccine adjuvants and excipients. In: Powell M F, Newman M J eds. <<Vaccine design: the subunit and adjuvant approach>>. New York: Plenum publishing, 1995: 141-228).)

Generally, adjuvants that may be comprised in a vaccine composition according to the invention encompass, without being limited to:

(i) Gel-type adjuvants, such as aluminium hydroxide or aluminium phosphate (Glenny A T et al., 1926; J Pathol Bacteriol; Vol. 29: 38-45; Gupta R K and Siber G R, 1994; Biologicals; Vol. 22: 53-63);

(ii) Microbial adjuvants, such as:
DNA CpG motifs (Chu R S et al., 199; J Exp Med; Vol. 186: 1623-1631); Monophosphoryl lipid A (Schneerson R et al., 1991; J Immunol; Vol. 147: 2136-2140); Cholera toxin (Holmgren J et al., 1993; Vaccine; Vol. 11: 1179-1184; Okahashi N et al., 1996; Infect Immun; Vol. 64: 1516-1525);
*E. coli* heat-labile toxin (Lycke N et al., 1992; Eur J Immunol; Vol. 22: 2277-2281; de Haan L et al., 1996; Vaccine; Vol. 14: 260-266; Chong C et al., 1998. Vaccine; Vol. 16: 732-740);
*Pertussis* toxin (Roberts M et al., 1995; Infect Immun; Vol. 63: 2100-2108; Mu H H and Sewell W A, 1994; Immunology; Vol. 83: 639-645);
Muramyl dipeptide (Ellouz F et al.; 1974; Biochem Biophys Res Commun; Vol. 59: 1317-1325); Cohen L Y et al., 1996; Cell Immunol; Vol. 169: 75-84);

(iii) Oil-emulsion and emulsifier-based adjuvants, such as:
Freund's incomplete adjuvant (Dhiman N et al., 1997; Med Microbiol Immunol (Berlin); Vol. 186: 45-51; Putkonen P et al., 1994; J Med Primatol; Vol. 23: 89-94);
MF59 (Dupuis M et al., 1998; Cell Immunol; Vol. 186: 18-27; Kahn J O et al., 1994; J infect Dis; Vol. 170: 1288-1291; Oft G et al., 1995; Vaccine. Vol. 13: 1557-1562);
SAF (Allison A C; 1998; Dev Biol Stand; Vol. 92: 3-11; Gupta R K et al., 1993; Vaccine; Vol. 11: 293-306; Byars N E et al., 1994; Vacine; Vol. 12: 200-209);

(iv) Particulate adjuvants, such as:
Immunostimulatory Complexes (ISCOMs) (Putkonen P et al., 1994; J Med Primatol; Vol. 23: 89-94; Gupta R K et al., 1993; Vaccine; Vol. 11: 293-306; Sjolander A et al., 1997; Cell Immunol; Vol. 177: 69-76);
liposomes (Richards R L et al., 1998; Infect Immun; Vol. 66: 2859-2865; Fernandes I et al., 1997; Mol Immunol; Vol. 34: 569-576);
biodegradable microspheres (Men Y et al., 1996; Vaccine; Vol. 14: 1442-1450; Shahin R et al., 1995; Infect Immun; Vol. 63: 1195-1200;
saponins (QS-21) (Newman M J et al., 1992; J Immunol; Vol. 148: 2357-2362; Neuzil K M et al., 1997; Vaccine. Vol. 15: 525-532);

(v) Synthetic adjuvants, such as:
- nonionic block copolymers (Hunter R L et al., 1994; AIDS Res Hum Retroviruses; Vol. 10 (Supl 2); S95-S98; Newman M J et al., 1997; Mech Ageing dev; Vol. 93: 189-203);
- muramyl peptide analogues (Cohen L Y et al., 1996; Cell Immunol; Vol. 169: 75-84; Fast D J and Vosika G J, 1997; Vaccine; Vol. 15: 1748-1752; Bahr G M et al., 1995; Int J Immunopharmacol; Vol. 17: 117-131);
- polyphosphazene (Payne L G et al., 1998; Vaccine; Vol. 16: 92-98);
- synthetic polynucleotides (Johnson A G, 1994; Clin Microbiol Rev; Vol. 7: 277-289; Harrington D G et al., 1979; Infect Immun; Vol. 24: 160-166); and (vi) cytokines, such as:
- IFN-γ (Odean M J et al., 1990; Infect Immun; Vol. 58: 427-432);
- Interleukin-2 (Nunberg J et al., 1989; Proc Natl Acad Sci USA; Vol. 86: 4240-4243);
- Interleukin-12 (Luis C et al., 1994; Science; Vol. 263: 235-237 Bliss J et al., 1996; J Immunol; Vol. 156: 887-894; Jankovic D et al., 1997, J Immunol; Vol. 159: 2409-2417).

A further aspect of the present invention therefore relates to the use of a stable immunogenic product or of a vaccine composition as defined above to induce an immune response in a mammal including a humoral immune response wherein antibodies that neutralize the immmunosuppressive, apoptotic or angiogenic properties of the native cytokine.

A further object of the invention consists of a method for inducing the production of antibodies that neutralize the activity of native TNFα in a mammal, comprising a step of administering to said mammal (i) a vaccine composition as disclosed above or (ii) a stable immunogenic product comprising antigenic heterocomplexes of TNFα and a carrier protein as described above together with one or more immunoadjuvants.

The vaccine compositions optionally may include vaccine-compatible pharmaceutically acceptable (ie., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

A vaccine composition according to the invention may also further comprise one or more pharmaceutically acceptable carriers and/or diluents, such carriers include any carrier that does not itself induce the production of a response harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art.

The vaccine compositions according to the invention may typically also contain diluents, such as water, saline, glycerol, ethanol, etc. Additionally, auxiliary substances, such as wefting or emulsifying agents, pH buffering substances, and the like, may be present in the compositions.

Suitable preparations of the vaccines of the present invention include injectables, either liquid solutions or suspensions. Solid forms suitable for solution in, or suspension in, a liquid pharmaceutically acceptable carrier prior to injection may also be prepared. The vaccine preparation may be emulsified. Additional substances that can be included in a product for use in the present methods include, but are not limited to one or more preservatives such as disodium or tetrasodium salt of ethylenediaminetetracetic acid (EDTA), merthiolate, and the like.

The vaccine compositions optionally may include vaccine-compatible pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

The vaccine compositions can be packaged in forms convenient for delivery. The compositions can be enclosed within a capsule, caplet, sachet, cachet, gelatin, paper, or other container. These delivery forms are preferred when compatible with entry of the immunogenic composition into the recipient organism and, particularly, when the immunogenic composition is being delivered in unit dose form. The dosage units can be packaged, e.g., in tablets, capsules, suppositories or cachets.

The forms suitable for injectable use include sterile aqueous solutions (where water soluble) or dispersions and sterile powders for the extemporaneous preparation of sterile injectable solutions or dispersions. They must be stable under the conditions of manufacture and storage and must be preserved against the contaminating action of microorganisms such as bacteria and fungi. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active immunogenic compound according to the invention is suitably protected, it may be orally administered, for example, with an inert diluent or with an assimilable edible carrier, or it may be enclosed in hard or soft shell gelatin capsule, compressed into tablets, or incorporated directly with the food of the diet. For oral therapeutic administration, the active immunogenic compound according to the invention may be incorporated with excipients and used in the form of ingestible tablets, buccal tablets, troches, capsules, elixirs, suspensions, syrups, wafers, and the like. Such vaccine compositions and preparations should contain at least 1% by weight of active immunogenic compound. The percentage of the compositions and preparations may, of course, be varied and may conveniently be between about 5 to about 80% of the weight of the unit. The amount of active immunogenic compound in such therapeutically useful vaccine compositions is such that a suitable dosage will be obtained. Preferred vaccine compositions or preparations according to the present invention are prepared so that a dosage unit form contains between about 0.1 g and 2000 mg of active immunogenic compound.

A vaccine composition according to the invention suitable for oral administration may also be prepared under the form of a liquid solution, including a liquid aerosol formulation.

The liquid aerosol formulations contain the immunogenic product and a dispersing agent in a physiologically acceptable diluent. The dry powder aerosol formulations of the present invention consist of a finely divided solid form of the immunogenic product and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term “aerosol particle” is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art. In a particular embodiment, the mass median dynamic diameter will be 5 micrometers or less in order to ensure that the drug particles reach the lung alveoli [Wearley, L. L., Crit. Rev. in Ther. Drug Carrier Systems 8:333 (1991)].

Systems of aerosol delivery, such as the pressurized metered dose inhaler and the dry powder inhaler are disclosed in Newman, S. P., (Aerosols and the Lung, Clarke, S. W. and Davia, D. editors, pp. 197-22) and can be used in connection with the present invention.

The vaccine compositions according to the invention may be administered to the subject to be immunized by any conventional method including, e.g., by oral, intravenous, intradermal, intramuscular, intramammary, intraperitoneal, or subcutaneous injection; by oral, transdermal, sublingual, intranasal, anal, or vaginal, delivery. The treatment may consist of a single dose or a plurality of doses over a period of time.

The present invention is further illustrated by the figures and the examples below.

FIGURES

FIG. 1 consists of a scheme that illustrates the general procedure for manufacturing a stable immunogenic product according to the invention.

FIG. 2 illustrates the humoral response in mice immunized with (A) KLH alone or (B) a stable immunogenic product manufactured as disclosed in Example 1. Abscissa: individuals; Ordinate: IgG anti-TNFα antibody titers.

FIG. 3 illustrates the anti-TNFα neutralizing activity of the serum antibodies produced by mice immunized by (A) KLH alone or (B)) a stable immunogenic product manufactured as disclosed in Example 1. Each curve corresponds to the blood serum form one mouse. Abscissa: percent neutralization of the TNFα activity; Ordinate: serum dilution.

FIG. 4 illustrates the humoral response of Rhesus macaques immunized with (A) KLH alone, (B) 20 μg of) a stable immunogenic product manufactured as disclosed in Example 1, and (C) 80 μg of) a stable immunogenic product manufactured as disclosed in Example 1. Abscissa: Days after first injection; Ordinate: IgG anti-TNFα antibody titers.

FIG. 5 illustrates the anti-TNFα neutralizing activity of the serum antibodies produced by Rhesus macaques immunized with (A) KLH alone, (B) 20 μg of a stable immunogenic product manufactured as disclosed in Example 1, and (C) 80 μg of) a stable immunogenic product manufactured as disclosed in Example 1. Abscissa: percent neutralization of the TNFα activity; Ordinate: serum dilution.

FIG. 6 illustrates the humoral response of transgenic huTNFα B6.SJL-Tg(TNF) N2 mice immunized with (A) Control PBS buffer, (B) KLH alone, (C) of a stable immunogenic product manufactured as disclosed in Example 1 and (D) of a stable immunogenic product manufactured as disclosed in Example 1 combined with methotrexate. Abscissa: individuals; Ordinate: IgG anti-TNFα antibody titers.

FIG. 7 illustrates the arthritis clinical scores determined in transgenic huTNFα B6.SJL-Tg(TNF) N2 injected with NaCl [♦];

KLH alone [■];

a stable immunogenic product manufactured as disclosed in Example 1

[▲]; and a stable immunogenic product manufactured as disclosed in Example 1 combined with methotrexate [■]

Abscissa: Days after first injection; Ordinate: arthritis clinical scores.

FIG. 8. illustrates the characterization of hTNFα-Kinoid.

FIG. 8-*a*) 1: RPN800 MW markers, 2: KLH (0.8 μg), 3: hTNFα (0.8 μg), 4: 3 μg of kinoid loaded on 12% SDS-PAGE. Revelation by either silver staining or Western blotting.

FIG. 8-*b*) autoradiogram: 1: MW markers; 2: 125I-hTNFα; 3: kinoid labelled on hTNFα; 4: kinoid labelled on KLH; 5: 125I-KLH.

FIG. 8-*c*) Kinoid (50 μg) filtered on a superose 6 column (10×300). Elution at 0.2 ml with DBPS. Column was previously calibrated by applied a series of MW markers.

FIG. 8-*d*) Comparative evaluation of biological activity of TNFα (♦) and kinoid (◇) on L929 cells. e) Comparative binding of TNFα to receptor I (♦) and II (▲) and kinoid to receptor I (◇) and II (□).

FIG. 9 illustrates the antibody response in TTg and Balb/c mice.

FIG. 9-*a*) Serum anti-TNFα Ab Titer in kinoid, inactivated TNFα (iTNFα) or KLH immunized TTg compared to Balb/c mice.

FIG. 9-*b*) to 9-*e*): Evaluation in kinoid (◇) and KLH (♦) immunized mice of FIG. 9-*b*) neutralizing capacity according to serum dilution, FIG. 9-*c*) serum neutralizing capacity as a function of time, FIG. 9-*d*) serum hTNFα binding inhibition to receptor I, FIG. 9-*e*) IgG neutralizing capacity, FIG. 9-*f*) IgG inhibition of binding to TNFα receptor I.

1-immunization regimen: 2 i.m. injections of 20 μg 3 weeks apart and boostering (5 μg at 6 weeks); 2: 2 i.m. injections of 10 μg and a boost of 5 μg.

FIG. 10 illustrates the cell-mediated immunity of mouse splenocytes to hTNFα.

Purified splenocytes from KLH (n=3) (♦) and kinoid (n=2) (◇) immunized mice. Balb/c and TTg mice were immunized on days 1, 8, 29. A boost was performed on day 90 and spleens were harvested at sacrifice (day 120). Splenocytes were stimulated in vitro for 96 hr with a) hTNFα, b) murine TNFα (muTNFα) and c) KLH antigen. Specific cell proliferation was measured either by 3H-Thymidine incorporation and expressed as stimulation index (FIG. 10-A) or IL2 (FIG. 10-B) and IFN-γ (FIG. 10-C) production in the culture supernatant after 44 h and 72 h respectively (see materials and method section).

Figure 11:
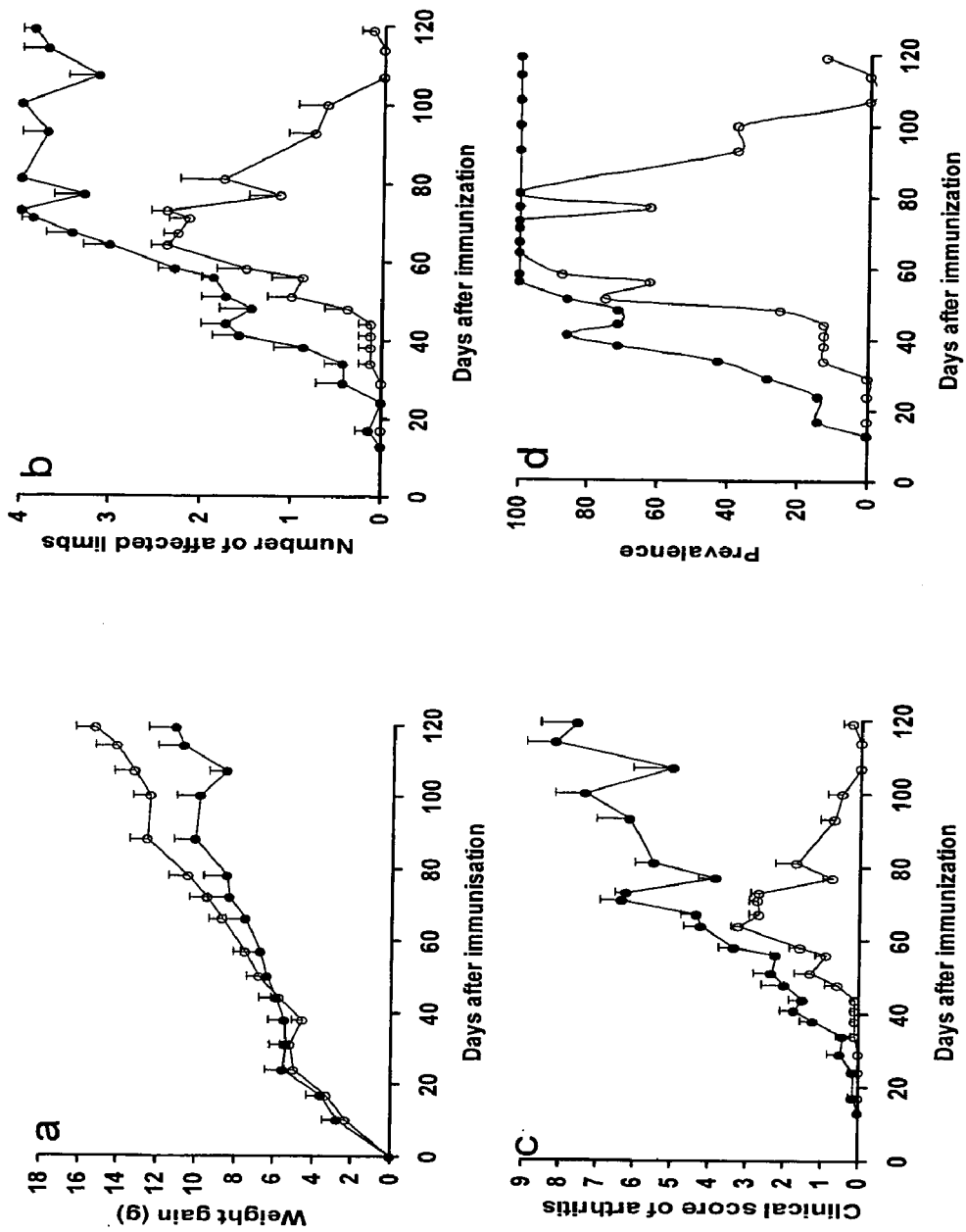

FIG. 11 shows that a vaccination with hTNFα kinoid improves clinical arthritis in hTNFα transgenic mice.

Seven week old mice were immunized on days 1, 7, and 28 with KLH-TNFα (open circles) (n=8) or KLH (closed circles) (control group, n=7). Differences between the groups were statistically significant for any parameter:

FIG. 11-*a*): Evolution of weight gain from the start of experiment. P<0.05 (ANOVA);

FIG. 11-*b*): Number of affected limbs. P<0.0001 (ANOVA);

FIG. 11-*c*): Clinical scores of arthritis P<0.0001 (ANOVA);

FIG. 11-*d*) Daily prevalence of arthritis (percent) showing the regression of the disease in vaccinated groups (P<0.01, ANOVA).

This experiment was repeated twice with similar results.

EXAMPLES

Examples 1 to 7

Example 1

Method of Manufacturing a Stable Immunogenic Product According to the Invention

A. Materials

TABLE 1

Chemicals and Reagents

| Reagent | Grade | Supplier | Details | Application |
|---|---|---|---|---|
| Glutaraldehyde 25% | Grade 1 | Sigma | G5882 10 × 1 mL | PD & GMP |
| Formaldehyde 37% | — | Sigma | F-1635 25 mL | PD |
| Formaldehyde 37% | EP | Sigma | 15513 | GMP |
| Di-sodium hydrogen phosphate (anhydrous) | Analar | BDH | 10249 | PD |
| Di-sodium hydrogen phosphate (anhydrous) | USP | Merck | 1.06585 5 kg | GMP |
| EDTA | Analar | BDH | 10093 | PD |
| EDTA | USP | Merck | 108421 1 kg | GMP |
| Glycine | Analar | BDH | 10119 | PD |
| Glycine | USP | Merck | 500190 1 kg | GMP |
| Sodium chloride | Analar | BDH | 10241 | PD |
| Sodium chloride | BP | Merck | 116224 | GMP |
| DMSO | 99.5% | Sigma | D5879 | PD |
| DMSO | USP | Sigma | D2438 10 mL | GMP |
| DPBS | — | Sigma | D8537 | PD |
| DPBS | tbc | tbc | tbc | GMP |

TABLE 2

Consumables

| Description | Supplier | Application |
|---|---|---|
| Slide-a-Lyzer ® cassettes 7 kDa MWCO (0.5-3 mL) | Perbio; 66370 | Dialysis |
| Pellicon XL PES membranes (5 or 10 kDa MWCO) | Millipore; PXB010A50 | Tangential flow filtration |
| 50 mL tubes | Nunc; 362696 | Sample container |
| Wide mouth polypropylene bottle (150 mL) | VWR; 215-0520 | Sample container |
| Wide mouth polypropylene bottle (250 mL) | VWR; 215-5683 | Sample container |
| Cryovials (3.5 mL & 2 mL) | Sigma; V1138; V9637 | Sample container |
| Labscale TFF unit with 500 mL acrylic reservoir | Millipore; XX42LSS13 | Tangential flow filtration |

B. Description of the Method

The process disclosed in this example illustrates an embodiment of the method according to the invention for manufacturing a stable immunogenic product comprising antigenic heterocomplexes of TNFα and KLH.

Further, the method which is detailed hereunder is designed for manufacturing a batch of 120 mg of the stable immunogenic product.

Step a)

Take 30.05 mL of TNFα (at 4.2 mg/ml) and allow to thaw at 4° C. overnight (NB: 126.21 mg of TNFα required).

Step b) (or Step b1) in Certain Embodiments of the Method)

Add 90.15 mL of "dilution buffer" to obtain the "working buffer" solution and TNFα at 1 mg/mL (±10%).

Dilution buffer=130 mM di-sodium hydrogen phosphate, 133 mM NaCl, 6.6 mM EDTA, pH 7.8.

Working buffer=100 mM di-sodium hydrogen phosphate, 150 mM NaCl, 5 mM EDTA, pH 7.8.

Step b2)

To the remaining 120 mL of the TNFα at 1 mg/mL (±10%) and add 1.2 mL of DMSO. Hold the mixture at RT for 30 minutes. Mix by agitation every 10 minutes and attempt to avoid foam formation.

Add 61.34 mL of "working buffer" to the mixture. Mix gently by inverting the container and attempt to avoid foam formation.

Step c)

Add 51.6 mg of KLH. Note: for a 9.81 mg/mL solution of KLH add 5.26 mL. Mix gently by inverting the container. The total volume at this point is 187.8 mL.

Step d)

Dilute the 25% stock of glutaraldehyde to 2.5% using the "working buffer". This is done immediately prior to use.

Add 20.86 mL of the diluted 2.5% solution of glutaraldehyde. Note that the total volume at this point is 208.56 mL. Mix gently by inverting the container.

Close the bottle and incubate for 45 min at RT. Gentle turn the bottle over every 15 min.

Step e) Diafilter the Solution Using Tangential Flow Filtration (TFF) Against the Working Buffer.

dialysis three times against 20 volumes of phosphate buffer at pH 7.6 10 mM, 150 mM NaCl.

Volume 1=2 hours

Volume 2=2 hours

Volume 3=overnight

Step f)

Dilute stock solution of formaldehyde (at 37%) 10-fold with "working buffer" to give a 3.7% solution. This is done immediately prior to use.

Add diluted 3.7% formaldehyde to the TNFα-KLH solution to give a final concentration of 0.2%.

For example, if the volume recovered is 200 mL, then the amount of 3.7% formaldehyde to be added will be 11.43 mL).

Seal the bottle and incubate for 6 days at 37° C. The bottle is overturned once a day.

Step g)

After the 6 days, add 2M glycine (made up in WFI) to a final concentration of 0.1M. Incubate for 1 hr at RT during which the bottle is gently overturned.

Step h)

Check the pH of the DPBS (Sigma) to be used for diafiltration and adjust if required to a final pH of 7.3±0.2 using 0.1M NaOH. No need for pH adjustment is normally expected.

Diafilter the solution using Tangential Flow Filtration (TFF) against DPBS.

2×5 kDa MWCO TFF membranes will be used

A 500 mL (acrylic) reservoir on the Labscale TFF system will be used.

Material is recovered from the membrane by draining the concentrate (ultrafiltration retentate) into a pre-weight polypropylene bottle.

Example 2

Test Procedures for the Stable Immunogenic Product Obtained by the Method According to the Invention The test procedures disclosed in Example 2 may referred to by the one skilled in the art. However, the one skilled in the art may also perform test procedures according to any one of the test procedures that are disclosed in the various examples herein.

2.1. Total Protein Content Determination by Colorimetry: Example of the Bradford Test The protein content is determined using the Bradford technique (Bradford, M. Anal. Biochem. 1976. 72, 248-254).

Briefly, a calibration curve is established with bovine serum albumin (BSA) by pipetting in a series of test tubes 0, 10, 20, 30, 40 μL of a 0.2 mg/mL BSA solution in PBS. Subsequently, the volume of each tube is completed to 500 μL by adding the corresponding volume of DI water. To each tube is then added 500 μL of Bradford reagent. Two blanks are prepared with 200 μL PBS. After 5 min. reaction at room temperature, the content of each tube is vortexed and read at 595 nm.

Two hundred μL of an appropriate dilution of the test protein solution are reacted with the Bradford reagent as described above.

TNFα Protein Content in KLH-TNFα: ELISA

Four samples of KLH-TNFα taken from 4 vials are diluted in Phosphate Buffered Saline pH 7.2 (PBS) at 5 μg/mL. These dilutions are used for coating microtiter plates (Costar 3590), 100 μL per well. After allowing coating to occur overnight at 4° C., the plates are washed with PBS containing 0.1% Tween 20 and the wells are saturated with 2% Fetal Calf Serum (FCS) solution in 100 μL PBS-Tween for 2 hr at 37° C. After washing the plates with PBS-Tween, 100 μL of serial dilutions of an anti-TNFα serum are pipetted into each well and the plates are incubated for 2 hr at 37° C., after which they are thoroughly washed and again incubated for 2 hr at 37° C., after adding to each well 100 μL of a HRP-labelled anti-IgG antiserum.

Following incubation, the plates are washed and 100 μL of ortho-phenylenediamine (OPD) solution are added to each well. Three minutes later, 100 μL of 2N sulphuric acid are added to each well and the plates are read at 490 nm in a multiscan photometer.

2.2. Purity Grade of KLH-TNFα Immunogen: IEF+Western Blot

The purity grade of the immunogen is assessed by isoelectric focusing (IEF) by allowing the KLH-TNFα immunogen to migrate aside KLH alone and TNFα alone on a 1% agarose plate in a 3 to 10 pH gradient. After applying an appropriate dilution of each sample at 250 μg/mL, the migration is carried out using a Phast system apparatus (Amersham Pharmacia) under the following conditions:

1st step (pre-migration): 500 V, 2.5 mA, 2.5 W, 15° C., 5 aVh

2nd step (application): 200 V, 2.5 mA, 2.5 W, 15° C., 5 aVh

3rd step (migration): 1500 V, 2.5 mA, 2.5 W, 15° C., 450 aVh

Following migration, the proteins are transferred by microcapillarity to a PVDF membrane and the proteins are revealed by Western Blot.

Western Blot Detection

The nitrocellulose membrane is saturated by dipping it overnight in 5% milk-TBS Tween 20 at room temperature, after which it is incubated for 1 hr with either the primary polyclonal anti-TNFα (hu) or anti-KLH antibody diluted in 10% milk-TBS Tween 20 at room temperature. Subsequently, the membrane is washed 4 times during 5 min with TBS-Tween 20 before being incubated for 1 hr with the secondary HRP-labelled antibody diluted with 10% milk-TBS Tween 20 at room temperature. Again, the membrane is washed 4 times with TBS-Tween 20 and the spots are revealed by chemo-luminescence using an ECL Plus Kit (Amersham Pharmacia).

3. Percentage of TNFα-KLH Covalent Bonds in the Stable Immunogenic Product 3.1. Method N° 1: Size Exclusion Chromatography in Denaturing and Reducing Conditions.

The test kinoid solution is submitted to denaturing (urea 8M final concentration) and reducing (beta-mercaptoethanol 5% final concentration) conditions that will lead to a dissociation of noncovalent bonds. The resulting solution is eluted through a size-exclusion column packed with Superdex 200™ (Pharmacia), chosen for its 600 kDa fraction limit, far below the molecular weight of KLH and covalent KLH-TNFα constructs. Only those cytokine molecules covalently linked to KLH will be present in the exclusion volume. The latter is assayed for TNFα (specific TNFα antigens) using a sandwich-ELISA technique with anti-TNFα Abs that have no cross-immune reaction with KLH. The result is expressed as a percentage of TNFα titer in the starting solution, which is measured by the same ELISA technique. This percentage is equal to the % TNFα-KLH covalent bonds in the TNFα kinoid.

3.2 Method N° 2: Double-Sandwich ELISA with Tween Washing

A 1 mg/mL solution of anti-KLH polyclonal Abs in PBS (10 mM pH 7.3 NaCl 150 mM) is used for coating a microtiter plate (Costar, high-binding), 100 µL per well, for 2 hr at 37° C. After 3 washing cycles with PBST (PBS with Tween 20 0.1% v/v), the wells are saturated for 1 h 30 with PBS containing 2% FCS. The wells are again washed 3 times with PBST.

Two identical series of dilutions of the test kinoid (10, 5, 0.156 µg/mL) are then added in the wells and incubated for 2 hr. The wells are washed 3 times with PBST, the dissociation action of which (via Tween 20) eliminates all molecules non-covalently bound to KLH, the latter KLH being fixed to the support-coated capture Abs. The first series of test dilutions is incubated with anti-KLH Abs while the second series is incubated with anti-TNFα Abs. After incubating for 1 h 30 at 37° C., wells are washed as described above, then incubated with specific peroxidase-coupled secondary Abs.

The addition of OPD, the peroxidase substrate, allows a quantitative colorimetric detection of the fixed anti-TNFα Abs, for the first series, and fixed anti-KLH Abs, for the second series. The ratio of fixed Abs between the two series gives the percentage of TNFα covalently bound to KLH in the kinoid.

4. Immunological Activity of KLH-TNFα Kinoids Antigenicity Test: ELISA

This test is intended for measuring the capacity of an immunogen (either an antigen derivative, or an antigen bound to a carrier protein) to combine with a specific antibody with respect to that of the native antigen. This test essentially consists in a reverse ELISA.

A series of increasing dilutions of the immunogen under test are distributed into wells of a polystyrene microtiter plate. A specific polyclonal antibody directed to the protein to be tested is allowed to react with the immunogen immobilized in the wells. After removing the excess of antibody unreacted by washing the plate, the Ab immobilized by the immunogen in the wells is quantitatively revealed by having it reacted with a HRP-labelled Ab directed to the first Ab, the yellow colour that develops by adding an appropriate substrate is directly proportional to the amount of immobilized protein. The optical density (OD) of each well is measured with an absorbance microplate reader. The protein content in the test sample is determined from a calibration curve.

5. Immunogenicity of Kinoids

The immunogenicity of an immunogenic preparation is:
1 its capacity level to induce the formation of specific anti-TNFα polyclonal Abs (measured in vivo); and
2 the neutralization capacity thereof. The latter is measured in vitro by quantifying the capacity of the antiserum, sampled from the immunized mice, to inhibit the specific biological activity of TNFα

1 For this, groups of 20 7-week-old Balb/c mice, 18-20 g body weight, housed in separate cages of 5 animals, fed with standard diet in pellets with food and water ad libitum are immunized on day 0, 7, 14 and 21 by intramuscular administration of 0.1 mL (10 µg) of the test immunogen in ISA 51 (1:1 v/v emulsion in ISA 51). A booster injection of 5 µg of the immunogen is given as 0.1 ml of a 1:1 emulsion in ISA 51 on day 60. A blood sample is taken 2 days before initiating the immunization by retro-orbital puncture and again 12 days after the last injection for antibody level determination by ELISA. Three control mice receive a 1:1 v/v emulsion of PBS in IFA.

Serum Ab titers are expressed as the inverse of the dilution that gives an OD>0.3.

6. Immunotoxicity—In Vitro

Test of proliferation (by incorporation of 3H-thymidine) of T cells stimulated by PPD/TT antigens and treated with various kinoid doses. PBMC's are freshly isolated from healthy donors by blood separation by Ficoll gradient centrifugation. Cells are introduced in round-bottom 96-well plates, 15,000 cells/well in RPMIc medium with 10% FCS. The kinoid is added at concentration 1 µg/mL to 100 ng/mL, then PPD or TT at 0.16%. Plates are allowed to incubate at 37° C. 5% CO2 for 6 days. Tritiated thymidine is added 18 hr prior to incubation end, 0.5 µCi/well. Cell proliferation is analysed with a β scintillation counter.

7. Biological Characteristics of KLH-TNFα Kinoids TNF-α Bio-Assay:

Cytolysis of Murine L929 Cells in the Presence of Actinomycin D

Materials

L929 mouse fibroblast line (ATCC Cat. No. CCL-1) KLH-TNFα (murine or human) kinoid in PBS (standard), NEOVACS Recombinant murine TNFα Peprotech (315-01A) or human TNFα Peprotech (300-01A) Culture Medium (RPMI supplemented with 10% FCS (Foetal Calf Serum) 2 mM glutamine, 100 U/ml penicillin-streptomycin Assay Medium (RPMI supplemented with 2% FCS 2 mM glutamine, 100 U/ml penicillin-streptomycin)

Pre-incubation medium: HL1 supplemented with 2 mM glutamine, 100 U/ml penicillin-streptomycin 96-well flat-bottom culture plate (Costar, 3595)

Actinomycin D, 1000 µg/mL stored at 4° C. (protected from light)

MTT solution (Sigma, M5655) 5 mg/mL stock in PBS stock aliquot kept at minus −20° C. (protected from light)

DMSO (SIGMA, 471267)

Experiment Duration 24-hour incubation 1 hour assay preparation

Method

1. Dilute KLH-TNFα murine or human kinoid and standard in a series of two-fold dilutions in the Assay Medium in 50 µL/well in 96-wells plate from row 2 to 11, starting at the proper dilution Leave row 1 as blank.

2. Prepare L929 cell suspension at a density of 7.5 105/mL in Assay Medium supplemented with actinomycin D at 1 µg/mL (protected from light). Add 50 µL/well of the cell suspension to the same plate, from row 1 to 12.

3. Incubate plate for 24 h at 37° C. 5% CO2 in a humidified incubator.

4. Rinse 2 times with PBS without Ca2+ Mg2+

5. Add 50 µL/well MTT solution at 40% in Assay Medium and incubate for 4 hours at 37° C. 5% CO2 in a humidified incubator.

6. Empty plates and add 50 µL of DMSO to each well.

7. Read plate at 550-630 nm

8. Analyse data.

Example 3

Comparative Study of the Various Preparation of KLH-TNFα (Human) Kinoids

Various preparation of a human TNF-α kinoid consisting of human TNF-α complexed to the specific carrier protein KLH have been performed.

More precisely, various preparations of KLH-TNFα (human) have been produced by the same general process that is disclosed in example 1 but with variations in (i) the percentage of DMSO, (ii) glutaraldehyde concentration (2.5 or 22.5 mM) as well as (iii) the time period of incubation of the intermediate product with formaldehyde (from 0.2 to 6 days incubation time period).

Then, the loss of the biological activity of the human TNF-α has been assayed. Also, the preservation of the conformational B-epitopes in the final kinoïd product has been tested through (i) the cytotoxicity assay of human TNFα on the L929 cell line, as well as (ii) through the immunogenicity assays disclosed herein in this example.

A. Materials and Methods

A.1 Assays for the Absence of TNFα Biological Activity in the KLH-TNFα (Human) Kinoids.

Human TNFα, in the presence of D actinomycin, possesses a cytotoxic activity on the murine fibroblast cells of the L929 cell line, which cytotoxic activity is assessed by the cell viability test using MTT (3-[4,5-dimethylthiazol-2-yl]-2,5-diphenyl-tetrazolium bromide. This assay is based on the MTT reduction by the mitochondrial NADPH reductase of the living cells towards the reduced product formazan which has a purple-blue color.

In this assay, the metabolic activity of the cells allows the evaluation of their viability.

The assessment of the biological activity of the KLH TNF-α kinoïds consists of incubating the L929 cells in the presence of decreasing amounts of said kinoïd product (50 ng/ml to 0 ng/ml) in combination with D actynomycin (1 µg/ml) in flat-bottomed wells of a microculture plate.

The cell culture is then performed at 37° C. in a wet atmosphere containing 5% $CO_2$ during a time period of 24 hours.

After a 24 hours culture time period, the cell culture supernatants are discarded and replaced by the MTT assay solution.

After 4 hours time period incubation at 37° C. with MTT, MTT solution is removed and DMSO is added.

After homogenisation, the optical density of the cell culture supernatant is analysed with a spectrophotometer at a wavelength of 570 nm.

The results are expressed as optical density (O.D.) at 570 nm. In parallel, cell cultures incubated with a range of TNFα from 0 to 10 ng/ml is performed, as a control.

The final results are expressed as lethal dose 50, also termed $LD_{50}$, which is the dose that induces the lysis of 50% of the cultured L929 cells.

A.2 Assay for the Preservation of the Conformational B-Epitopes of Human TNFα in the Final KLH-TNFα (Human) Kinoïds, After the Chemical Treatments with Glutaraldehyde and Formaldehyde: Immunogenicity Assay.

The study of the preservation of the conformational of B epitopes of the human TNFα in the final KLH-TNFα (human) kinoïds, after the chemical treatments, is performed by a test of the immunogenic activity in C57Bl/6 weighing 18-20 g.

At Day 0, a group of tree mice is injected with 0.2 ml (50 µg) of an emulsion in Complete Freund Adjuvant (CFA) by the intramuscular route A second injection of 25 µg of the kinoïd product in incomplete Freund adjuvant is administered at Day 21.

Retro-orbital blood sampling is performed on each mouse before the first injection and also at Day 28. Sera from each group of mice are gathered.

The humoral response is measured through detection of IgG isotype antibodies directed against human-TNFα in the sera of the immunized mice. The humoral response is determined by an ELISA assay and is expressed in antibody titers (dilution$^{-1}$ giving an optical density greater than 0.3).

The neutralizing capacity of the sera from mice immunised with the KLH-TNFα (human) kinoïds has been measured through the TNFα cytotoxicity assay on L929 cells, as described hereafter.

L929 cells are treated with various dilutions from pools of sera (dilutions from 1/100 to 1/12800) that have been sampled at Day-2 and Day 28 and then have been incubated during 40 minutes at room temperature, and then 20 minutes at 4° C. with 20 ng/ml of human TNFα.

The cell culture is pursued at 37° C. in wet atmosphere, 5% $CO_2$, during 24 hours.

After a 24 hours cell culture time period, the cell culture supernatants are removed and replaced by MTT solution.

After a 4 hours incubation at 37° C., MTT is removed and DMSO is added.

After homogenisation, the optical density of the cell culture supernatant is analysed with a spectrophotometer at the wavelength of 570 nm.

The results are expressed as optical density (O.D.) of the cell culture supernatants. A cell cultures incubated with a range of TNFα from 0 to 10 ng/ml is performed in parallel, as a control.

The sera that neutralize the cytotoxic activity of TNFα prevent to exert its cytotoxic activity on the L929 cells.

The results are expressed as the neutralizing capacity 50%, or $NC_{50}$, which corresponds to the sera dilution that neutralises 50% of the cytotoxic activity of the human TNFα.

B: Results

Table 3 hereunder discloses the results obtained with the final KLH TNFα (human) kinoïds prepared according to various chemical treatments.

TABLE 3

| Code | Glutaraldehyde (mM) | Formaldehyde (day) | EDTA | DMSO (%) | $ED_{50}$ (ng/ml) | Antibody titer | $NC_{50}$ |
| --- | --- | --- | --- | --- | --- | --- | --- |
| K1 | 2.5 | 2 | 5 mM | 0 | 12.5 | >64000 | 1/650 |
| K2 | 2,.5 | 2 | 5 mM | 2 | 20 | >64000 | 1/600 |
| K3 | 22.5 | 0 | 5 mM | 1 | 0.15 | >64000 | 1/600 |
| K4 | 22.5 | 2 | 5 mM | 1 | 200 | >64000 | 1/750 |
| K5 | 22.5 | 2 | 5 mM | 2 | 225 | >64000 | 1/400 |

TABLE 3-continued

| Code | Glutaraldehyde (mM) | Formaldehyde (day) | EDTA | DMSO (%) | ED$_{50}$ (ng/ml) | Antibody titer | NC$_{50}$ |
|------|---------------------|--------------------|------|----------|-------------------|----------------|-----------|
| K6   | 22.5 | 2 | 5 mM | 5 | 250  | >64000 | 1/700 |
| K7   | 22.5 | 6 | 5 mM | 1 | >400 | >64000 | 1/1200 |
| K8   | 22.5 | 6 | 5 mM | 2 | >400 | >64000 | 1/300 |
| K9   | 22.5 | 6 | 5 mM | 5 | >400 | >64000 | 1/350 |
| K10  | 22.5 | 2 | 0 mM | 0 | 15   | >64000 | 1/700 |

As shown in Table 3 above, the best results are obtained with a process of manufacturing KLH TNFα (human) kinoïd involving a chemical treatment (i) with DMSO at the concentration of 1% and (ii) with glutaraldehyde at the concentration of 22.5 mM, then (iii) with a chemical treatment with formaldehyde during the period of time of 6 days. The resulting final KLH-TNFα (human) product is devoid of the cytotoxicity activity of human TNFα and induces the production of polyclonal antibodies that neutralize the biological activity of the native human TNFα.

Thus, the manufacturing process according to the condition disclosed in K7 of table 3 above allows the inactivation of the human TNFα cytokine contained therein why preserving the conformational B-epitopes.

The KLH-TNFα (human) final product prepared according to the conditions named "k7" in Table 3 above is the same as the one which is manufactured according to example 1 above.

This best TNFα kinoid product is the one which has been studied in the following examples, notably in a transgenic mice model, in view of studying its ability to induce polyclonal antibodies that neutralize native TNFα in an autologous system.

Example 4

Study of the Acute Toxicity of the KLH-TNFα (Human) Kinoid in Mice

The goal of the study was to define the characteristic properties of a vaccine composition comprising a KLH-TNFα (human) kinoid according to the invention, to be used as a broad spectrum therapeutic vaccine for use in the treatment of cancerous cachexia and/or various auto-immune diseases (e.g. rhumatoïd arthritis, Crohn's disease and psoriasis).

Particularly, the vaccine composition properties as regards tolerance and absence of risk has been studied.

Consequently, a first toxicity study has been performed in SWISS mice.

A. Material and Methods

Fourty six (46) female SWISS mice have been distributed in (i) one group of four non-treated animals and (ii) three groups of fourteen animals that have received, respectively:
  a) Control Group (adjuvant vehicle): n=14
  An intramuscular route injection (IM) located in the thigh of phosphate buffer saline (PBS);
  The control group was used to assess the local and systemic reactivity of the adjuvant use in the formulation.
  b) Treated group (first dose: 2.000 times the single therapeutic human dose. STHD°/N+14.
  An intramuscular route injection (IM) located in the thigh of KLH-TNFα (human) kinoid at 50 µg/mouse in a phosphate buffer saline (PBS°;
  c) Treated group (second dose: 4000 times the single therapeutic human dose, STHD): n=14
  An intramuscular root injection (IM) located in the thigh of the KLH-TNFα (human) kinoid at the dose of 100 µg/mouse in a phosphate buffer saline (PBS).
  d) Group of naïve mice, non-treated, that were included in this study (n=4).

The computation of the dose concerns the single dose for human use, which is 80 µg/injection/individual: 1 SHTD (single therapeutic human dose), thus, 1.15 µg/kg.

The injections of the KLH-TNFα (human) kinoid have been performed at Day 5 (D 5) of the experimentation.

The response of animals to the treatment above has been tested according to the following parameters:
  a—The eventual number of death, immediate, short time period and long time period (observation period of 10 days after administration).
  b—Local or systemic reactivity to the treatment.
  c—Curve showing the general status and the weight of the animals until 10 days following administration of the KLH-TNFα (human) kinoid (D 15).

Five (5) days after the observation period (D20), the surviving animals have been sacrificed and the following controls have been performed.
  d—Microscopic anatomo-pathologic examination of the muscle at the location of the injection site, for evaluating the local tolerance.
  d—Determination of the weight of lungs, heart, liver and spleen, as an index value of the organ response to the administration of the immunostimulating substances.

B. Results

When administered to mice at highly elevated doses (about 4000 times the single human therapeutic dose in each mouse), the KLH-TNFα (human) kinoid has not led to any adverse effect, during the whole observation period of 10 days, and for each of the tested groups, as it is illustrated by:
  1) No occurrence of an immediate or medium term death;
  2) No local reaction at the site of injection, nor any systemic reaction;
  3) No effect on the growth curves of the mice, in any of the tested groups.

Further, the macroscopic examination of the organs from the animals sacrificed at the end of the test (D20) has shown no organ alteration nor any increase in the volume from the spleen and the liver.

Further, the weight of the heart, the lungs, the liver and the spleen have varied in a similar manner for the whole groups of animals tested.

Example 5

Study of the Immunogenicity of the KLH-TNFα (Human) Kinoid in a Transgenic Mice Model Suited for Human TNF The immunogenic activity (humoral) of the KLH-TNFα kinoid preparation, as compared with the immunogenic activity of the KLH, has been studied in mice B6.SJL-Tg (TNF) N2 of 5 weeks (group of 10 mice). These mice have been provided by Taconic Company (USA) and consist of mice which are transgenic for the human TNFα gene (hemizygote).

A. Material and Methods

At Day 0 and at Day 7, mice (group of 10 mice) have received an injection of 0.2 ml (30 µg) of an emulsion in ISA51 by the intramuscular root. A second injection of 25 µg in ISA51 was given at Day 28. Then, a retro-orbital blood sampling is performed in each mouse at Day 35.

B. Results

1. Humoral Response

Figure 2:
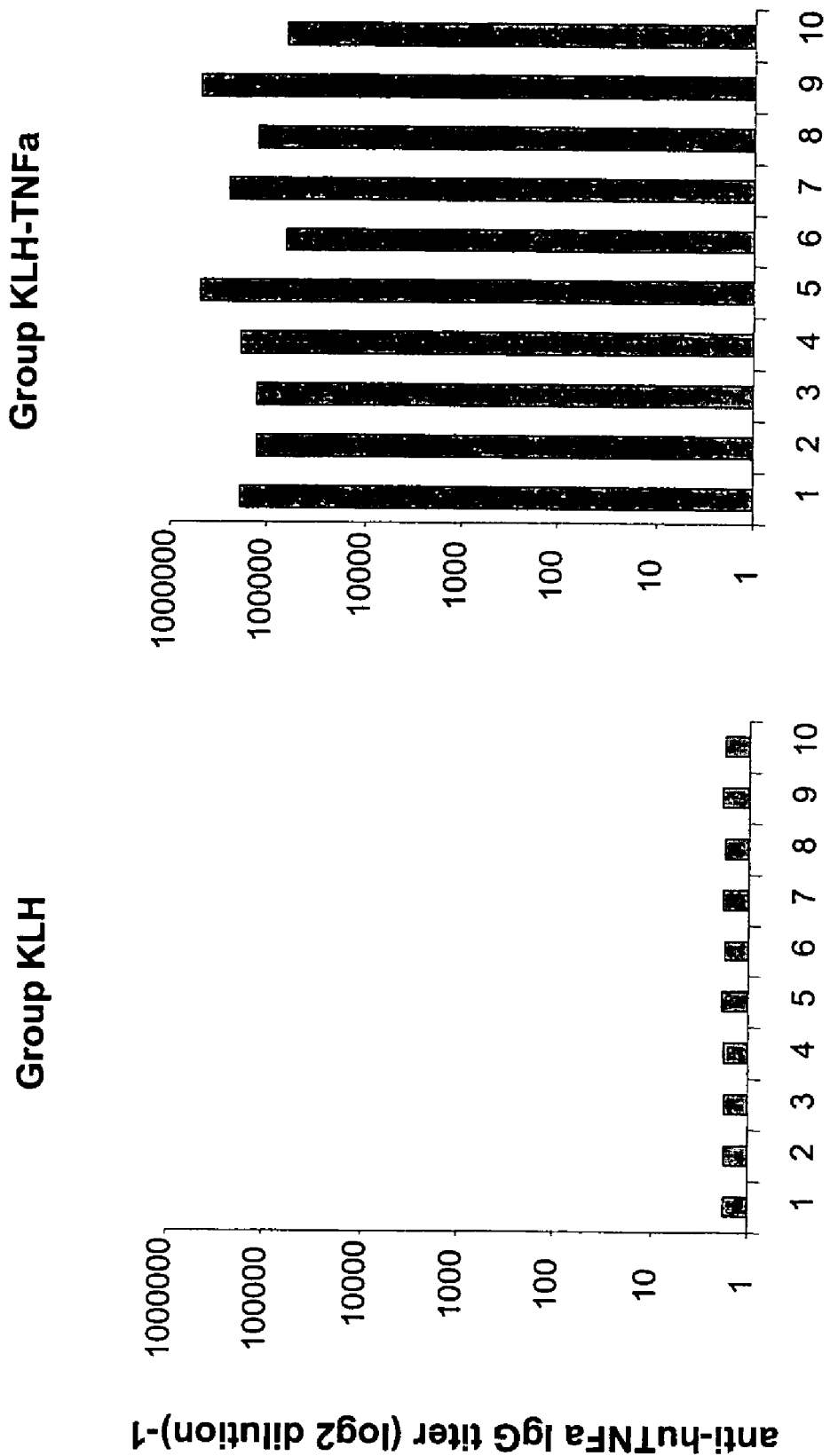

The humoral response is measured by the presence in the sera of the immunized mice of IgG type antibodies directed against human TNFα; The humoral response is determined by an ELISA assay and is expressed at the antibody titer (dilution$^{-1}$ giving an optical density greater than 0.3). FIG. 2 illustrates the antibody titre that were obtained.

The sera from mice immunised with the KLH-TNFα (human) final product obtained according to example 1 possess high level of IgG type antibody titers, whereas the sera from mice immunised with KLH are devoid of these antibodies.

Figure 3:
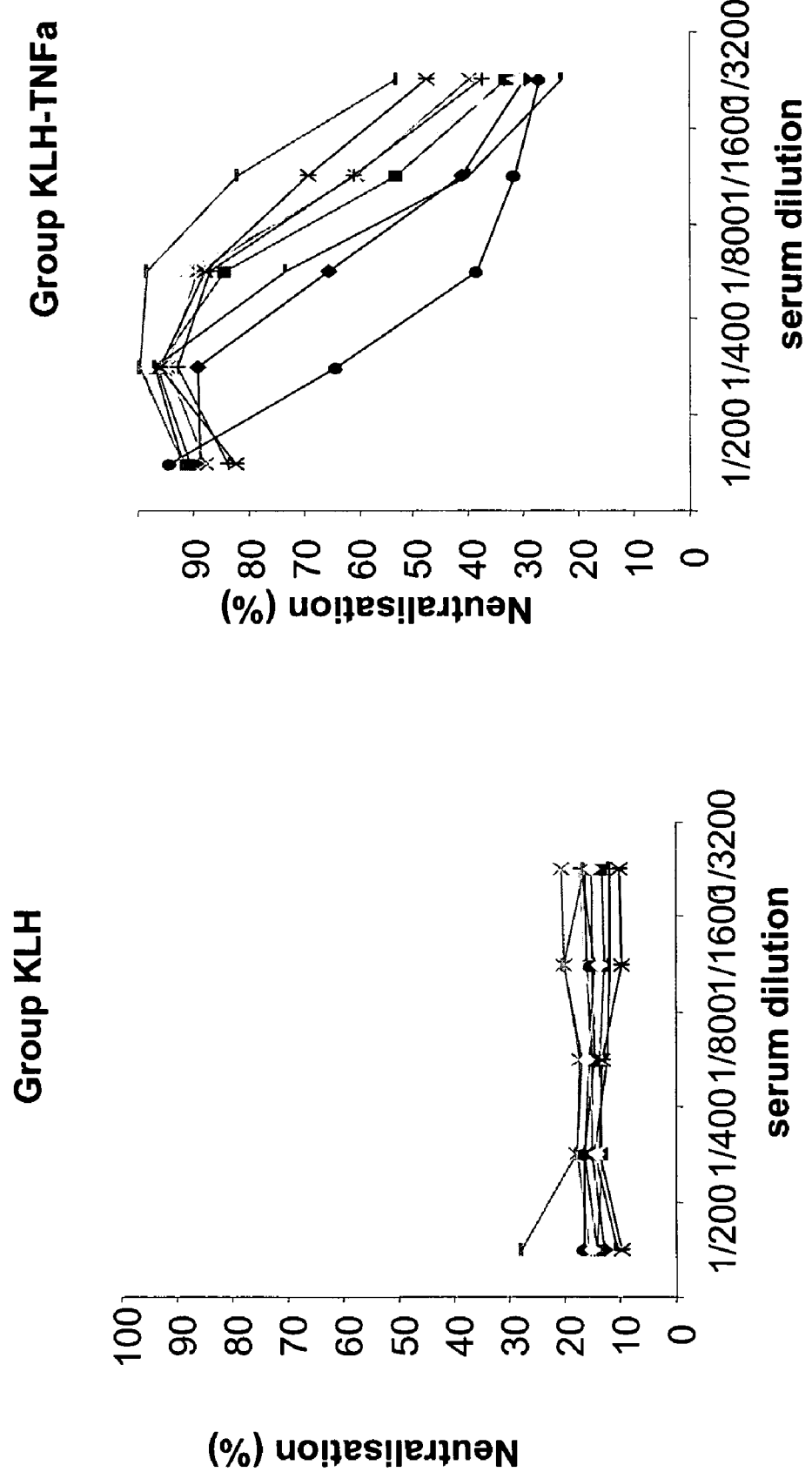

The neutralising activity of these antibodies has been measured with the TNFα cytotoxicity assay on L929 cells. The results are presented in FIG. 3.

The antibodies induced by the KLH-TNFα (human) kinoid preparation have a high level of neutralizing activity.

Example 6

Study of the Immunogenicity of the KLH-TNFα (Human) Kinoid in the Rhesus Macague The humoral immunogenic activity of the KLH-TNFα (human) kinoid as compared with the immunogenic activity of KLH alone, has been studied in rhesus macaque provided by MDS pharma (Lyon—France). It is to be noticed that the TNFα that is naturally produced by the macaque rhesus shares 98.1% aminoacid homology with human TNFα.

A—Material and Methods

At Day 0, Day 21 and Day 49, macaques have received an injection of 0.5 ml of an emulsion of the kinoid in ISA51 by the intramuscular route, containing (i) either 80 or 20 µg of the KLH-TNFα (human) kinoid preparation, or (ii) KLH alone. A blood sampling has been performed on each animal at Day 28, Day 56 and Day 68.

B—Results

Figure 4:
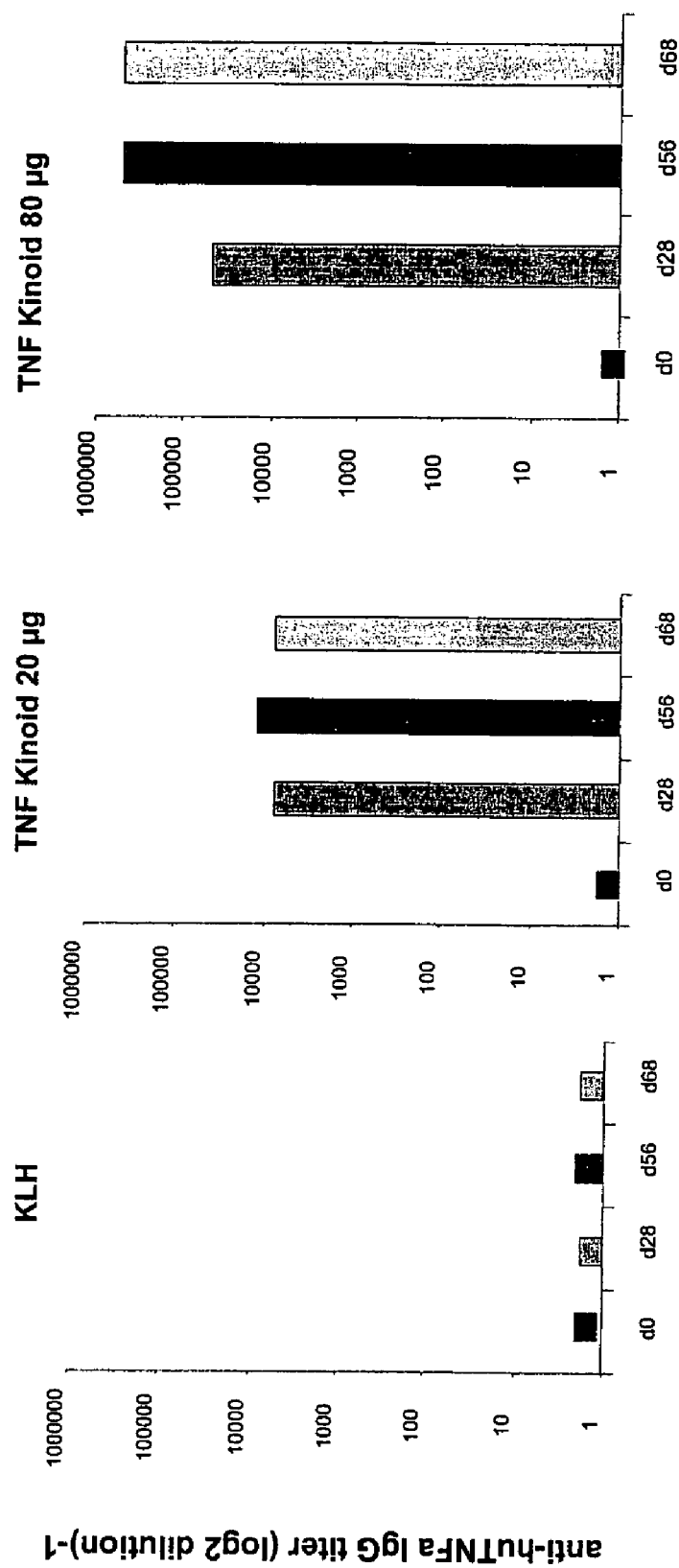

1—Humoral Response:

The humoral response has been measured by detecting the presence of IgG isotype antibodies directed against human TNFα in the sera of the immunized macaques. The humoral response has been determined with an ELISA assay and is expressed as antibody titers (dilution$^{-1}$ giving an optical density greater than 0.3). The results of the antibody titers obtained are reported in FIG. 4.

The sera from the macaques immunized with the KLH-TNFα (human) kinoid preparation have anti-TNFα IgG isotype antibody titers, whereas sera from the macaques immunized with KLH alone is devoid of these antibodies.

The anti-TNFα antibody titers are more important in the serum of the macaques that have received 80 µg of the KLH-TNFα (human) kinoid.

Figure 5:
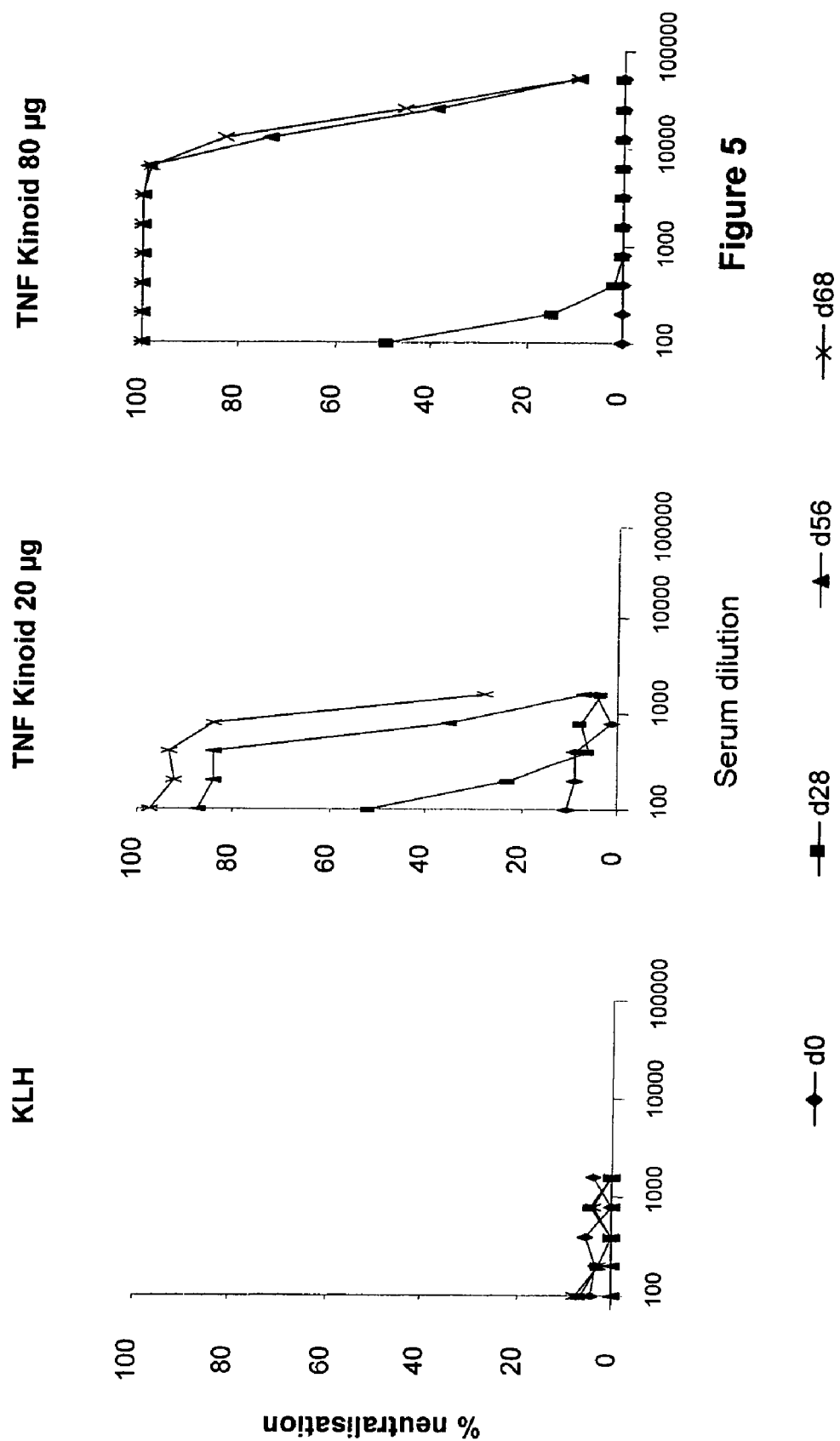

The neutralizing activities of the antibodies have been measured with the TNFα cytotoxicity assay on L929 cells. The results of these assays are reported in FIG. 5.

The antibodies induced by the KLH-TNFα (human) have a very high neutralizing activity.

Example 7

Assessment of the Therapeutic Efficiency of the Active Immunization Against TNFα in huTNFα Transgenic Mice The assessment of the therapeutic efficiency of the active immunization strategy against TNFα using the KLH-TNFα (human) kinoid preparation as the active ingredient have been performed in transgenic mice huTNFα B6.SJL-Tg (TNF) N2 of 5 weeks old, provided by Taconic Company (USA). These TNFα transgenic mice develop a spontaneous polyarthritis at the age of 4 to 5 weeks.

A—Material and Methods

1—Immunization.

Mice have received one injection of 0.2 ml of an emulsion in ISA51 by the intramuscular route at days D0, D7 and D28. Four groups of 10 mice have been treated as detailed hereunder:

Group A: PBS: 200 µl PBS
Group B: KLH: 200 µl KLH
Group C: KLH-TNF: 200 µl KLH-TNF
Group D: KLH-TNF+MTX: 200 µl KLH:TNF and methotrexate (1 mg/kg) three times a week, starting from immunization N° 1 and until sacrifice (intraperitoneal injection of 200 µl per injection).

Mice have received (i) at Day 0 and Day 7: 30 µg of the KLH-TNFα (human) kinoid preparation and (ii) at Day 28: 15 µg of the same preparation.

A retro-orbital blood sampling was performed on each mouse at Day 35. At Day 57, at the time the mice are sacrificed, a blood sampling has also been performed.

2—Clinical Examination and Quantitative Assessment of Arthritis:

A clinical examination has been performed, yet at the starting time of the experiment, and then twice a week.

The assessments were performed by an observer having no knowledge of the treatment that was applied. The clinical severity of arthritis at each joint (fingers, tarsus, ankle, carpe) was quantified by attribution of a score varying from 0 to 4 wherein: 0=normal; 1) erythema; 2=swelling; 3=deformation; and 4=major deformation or necrosis. A sum of these scores having performed in order to obtain an arthritis score for each animal, every day. A mean for each group was calculated for every day of treatment.

3—Histological Examination and Quantitative Evaluation of the Arthritis.

The animals were all sacrificed 57 days after the starting of the experiment. The posterior paws has been removed, fixed in formol, decalcified, then dehydrated and then included in paraffin blocks. Then, 5 µm thick histological slices were performed with a microtome. At least for serial sections were performed for each paw in order to ensure a correct spatial assessment of the joint affections. The slides preparations were then stained by hematoxylin and eosin and then observed under optical microscope. The lesions were quantitatively assessed on each section according to a three points scale (0=normal; 3=severe). This histological score may be divided into two parameters: destruction of the cartilage and of the bone (thickness of the cartilage and of the bone, irregularities and presence of erosions) on one hand, and on the other hand, inflammation (synovial proliferation, cell inflammatory infiltration).

4—Statistics:

The results values are given as mean and standard deviation from the mean (SDM). A student's t test as well as a variance analysis (ANOVA) have been performed.

B—Results:

1—Humoral Response:

The humoral response is measured by detecting the presence of IgG isotype antibodies directed against human TNFα in the sera of the immunized macaques. The humoral response is determined by an ELISA assay and the results are expressed as the antibody titer (dilution$^{-1}$ giving an optical density greater than 0.3).

Figure 6:
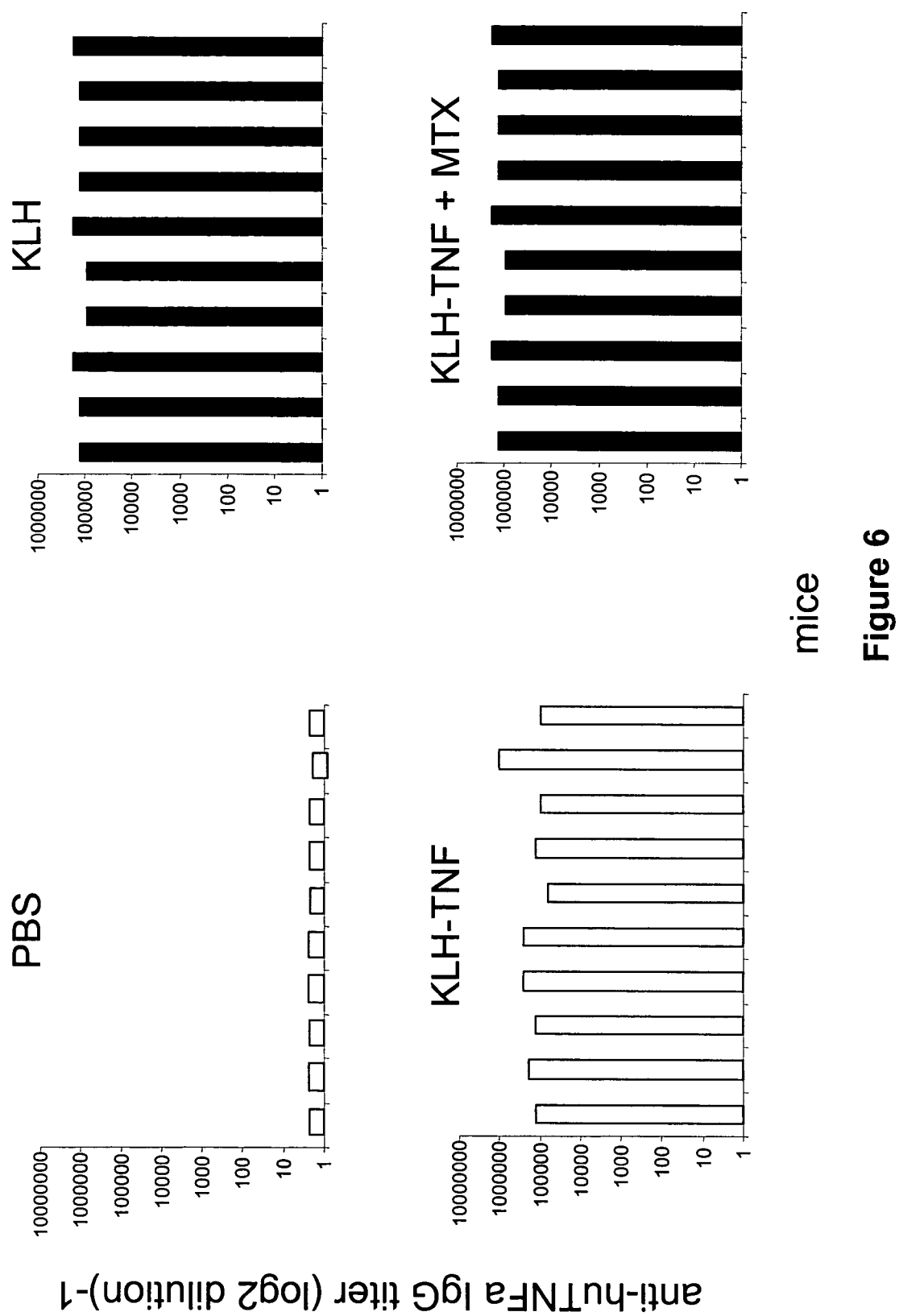

The results of the antibody titers that were obtained are reported in FIG. 6.

2—Clinical Examination and Quantitative Assessment of the Arthritis.

Evolution of the Clinical Score with Time.

Figure 7:
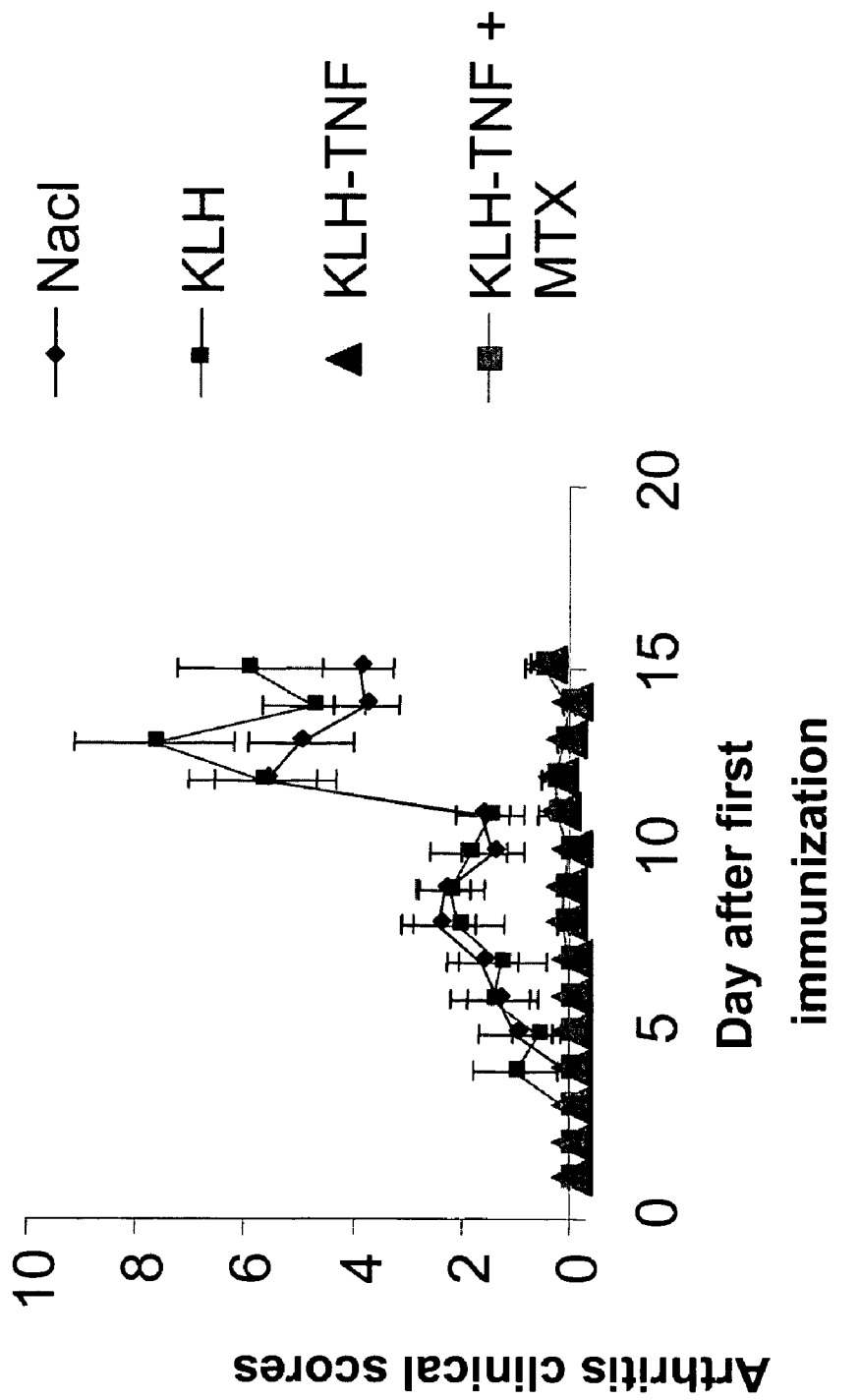

The evolution of the clinical score with time is reported in FIG. 7.

Treatment of the macaques (i) with KLH-TNF (human) kinoid or (ii) with KLH-TNF (human) kinoid combined with MTX induces a major statistically significant decrease of the arthritis scores that were assessed by clinical examination. By comparison, the arthritis scores determined for the control animals treated with KLH or with PBS buffer were far lower.

Assessment of the Disease Occurrence and Severity Occurrence Parameters

The assessment of the disease occurrence and disease severity is reported in table 4 hereunder.

The day of occurrence of the disease has been determined, for each animal, through a clinical examination. The animals that had never developed the disease were not taken into account The score "A MAX" corresponds to the maximal score reached by each animal during the experiment. The score "A MAX" represents a parameter of disease severity.

The incidence means the number of animals having developed arthritis before the end oft the experiment, it being taken into account the total number of animals in each group.

TABLE 4

| Treatment | Day of disease occurrence (sick animals only) | Amax Scores ± sted dev. | Incidence |
|---|---|---|---|
| PBS | 24.4 ± 2.5 | 11.5 ± 4.2 | 10/10 |
| KLH | 25.9 ± 2.5 | 9.0 ± 1.4 | 10/10 |
| KLH/TNF | 45 ± 2.3**/## | 0.9 ± 0.5**/# | 3/10 |
| KLH/TNF | 43.5 ± 3.3*/## | 1.0 ± 0.32**/# | 6/10 |

*p < 0.01 vs KLH
**p < 0.001 vs KLH
p < 0.02 vs PBS
p < 0.001 vs PBS (test t de Student)

The results show that the treatment by KLH-TNFα and by KLH-TNFα+MTX induces, in a statistically significant manner:
- a delay in the occurrence of the arthritis, as compared with the control animals treated by KLH alone or by PBS.
- a decrease in the severity of the arthritis; and
- a decrease in the number of sick animals.

3—Histological Examination and Quantitative Assessment of the Arthritis.

The results are reported in table 5 hereunder.

TABLE 5

| Treatment | Inflammation Scores ± sem | Destruction Scores ± sem |
|---|---|---|
| PBS | 1.30 ± 0.09 | 0.71 ± 0.11 |
| KLH | 1.53 ± 0.21 | 1.10 ± 0.23 |
| KLH/TNF | 0.16 ± 0,.09** | 0.08 ± 0,.03** |
| KLH/TNF | 0.24 ± 0.09** | 0.21 ± 0.12* |

*p < 0.01 vs KLH et vs PBS
**p < 0.001 vs KLH et vs PBS (Student's t test)

Treatment with KLH-TNF and with KLH-TNF+MTX induces, in a statistically significant manner, a decrease in the histological alterations (destruction and joint inflammation parameter).

C—Conclusion

Vaccination of the huTNFα transgenic mice with KLH-TNFα (human) kinoid preparation according to example 1 clearly protects the animals from inflammation and joint destruction, as it is shown by the results of the clinical and histological analysis.

The groups of animals treated with KLH-TNFα (human) kinoid preparation, as regards the joint protection, cannot be distinguished from the groups of animals treated with KLH-TNFα (human) kinoid preparation combined with MTX; These results may be explained by the fact that the major efficiency of the KLH-TNFα (human) kinoid alone masks, in these experimental conditions, the eventual beneficial effect of MTX.

The groups of animals treated by KLH cannot be distinguished from the groups of animals treated by PBS buffer.

Further results relating to the biological properties of the stable immunogenic product according to the invention are disclosed in the examples 8 to 12 hereunder.

Examples 8 to 12

A. Materials and Methods of Examples 8 to 12

A.1. Reagents.

KLH was purchased from Intracel (San Diego, Calif.), hTNFα from Boehringer Ingelheim (Mannheim, Germany), murine TNFα from Cytolab (Rehovot, Israel), hTNFα receptor RI and RII, hTNFα, murine IL2 and murine IFNγ ELISA kit from R&D system (Lille, France), ISA51 adjuvant from Seppic (Paris, France).

A.2. Animals.

4-5 week-old female and male heterozygous hTNF transgenic mice (1006-T) were purchased from Taconic, 6-8 week-old female C57Bl/6 and Balb/c mice from Charles River (L'Arbresles, France). Mice were maintained under pathogen-free conditions. Rabbits were maintained in Charles Rivers breeding (L'Arbresles, France) and *Macaca mulata* in MDSPharma Inc. (St-Germain-sur-L'Arbresles, France).

A.3. Preparation of Immunogen.

The hTNFα-KLH immunogen was prepared by performing the method disclosed in Example 1.

A.4. SDS/PAGE, Silver Staining and Immunoblotting.

SDS-PAGE analysis under non reducing conditions was carried out according to Laemmli (Laemmli, U. K. (1970), *Nature* 227: 680-85). On a 12% SDS-PAGE, the proteins were revealed by silver staining, autoradiography (Le Roy F., Bisbal C., Silhol M., Martinand C., Lebleu B. & Salehzada T. (2001). *The Journal of Biological Chemistry*, 276: 48473-482.) or immunoblotting analysis using the appropriate antibodies.

A.5. Gel-Filtration Chromatography.

The heterocomplex was loaded on a Superose 6 10/300 GL gel-filtration column (Amersham bioscience, Orsay, France) pre-equilibrated with DPBS and eluted with the same buffer as used for the equilibration, at 0.2 ml/min.

A.6. Cell Cultures.

Mouse L929 cell line (ATCC, CCL 1) was cultured in RPMI-1640 medium containing 10% FCS. Purified murine splenocytes were resuspended in RPMI medium containing 5% FCS and 50 µM 2-β-mercaptoethanol and incubated in culture medium with or without KLH (30 µg/ml), hTNFα (3 µg/ml) and murine TNFα (1 µg/ml) antigens.

A.7. T Cell Proliferation Assay.

Antigen activated splenocytes were cultured for 4 days and then pulsed for 18 h with 3H-Thymidine. Cells were harvested 18 h later on filter mats, and thymidine incorporation into DNA was quantified by using a beta counter. Stimulation index was expressed as: [(mean of cpm from stimulated cells)−(mean of cpm from unstimulated cells)]/(mean of cpm from unstimulated cells). SI values greater >2 were considered positive.

A.8. TNFα and Receptors Assays.

A.8.1. Direct Receptor Binding Assay:

The heterocomplex and hTNFα binding to their target receptors was measured using precoated plates with 50 ng/well of hTNFα RI or RII. Serial dilution of the samples were incubated with their receptor and bound hTNFα was detected using biotinylated goat polyclonal anti-hTNFα Ab (R&D Systems). To evaluate the capacity of serum or IgG to inhibit the binding of hTNFα to its receptor, hTNFα was first pretreated with serial dilution of tested sera or IgG before being transferred to the plate on to which hTNFα RI was immobilized. The blocking titer was expressed as the reciprocal of the serum dilution neutralizing 50% of hTNFα binding.

A.8.2. Anti-h TNFα Ab Titer Assay.

Specific anti-hTNFα Ab titer in sera of immunized and control mice was determined by a direct Elisa. Precoated Elisa plates with 50 ng/well hTNFα were incubated with serial silutions of sera from immunized and control mice. Specific IgG were detected using peroxidase Rabbit anti-mouse IgG (Zymed, Calif.). Endpoint titers were expressed as the reciprocal of the highest sample dilution giving an O.D. of 0.3.

A.8.3. Cytokine Quantification.

hTNFα, murine IL-2 and murine IFNγ were determined in the serum and culture supernatant by ELISA.

A.9. hTNFα Bioassay.

hTNFα activity was assessed using the L929 cytotoxicity assay (Bloquel 2004). Serial dilution of hTNFα and heterocomplex were incubated for 18 h with L929 cells in the presence of actinomycin D (1 µg/ml) and the number of surviving cells determined by the MTT assays. The ability of hyperimmune serum or IgG to neutralize hTNFα activity was similarly determined after incubating sera and IgG with hTNFα. The neutralizing titer was expressed as the reciprocal of the serum dilution which neutralizes 50% of hTNFα activity.

A.10. Immunization.

Animals were immunized by 3 or 4 times i.m. injections of ISA51-adjuvanted kinoid (Seppic) or control preparation (5-30 µg). Sera were collected 8 to 12 days after the $3^{rd}$ or $4^{th}$ immunization and at sacrifice.

A.11. Antibody Purification.

Immunoglobulin (IgG) and specific anti-hTNFα or anti-KLH antibodies were purified from immunized or control mice sera using a Protein G IgG purification kit (Pierce) or affinity chromatography on hTNF or KLH coupled Sepharose 4B columns (Sigma Chemical Co., St. Louis, Mo.). Avidity was determined using BIAcore 3000 technology (Lofas, S., Johnsson B. (1990) *J. Chem. Soc. Chem. Commun.* 21:1526; Karlsson, R., Falt A., (1997) *J. Immunol. Methods* 200:121).

A.12. Lethal Shock.

Control and hTNFα-kinoid immunized mice (C57Bl/6 or TTg) were IP challenged with hTNFα in presence of 20 mg of D-galactosamine in PBS 10 days after the last immunizing injection. A 80-90% lethal launching dose of hTNFα was administered Animal survival was recorded 24 hours post-injection (Lehmann V J Exp Med 1997 657). In these experiments, a macroscopic analysis of the liver was performed in a subgroup of mice sacrificed 8-hour post-TNFα administration.

A.13. Arthritis Follow-Up.

Human TNFα transgenic mice 1006-T develop a spontaneous arthritis from the $8^{th}$ week of age, as Tg197 strain (Keffer, J., Probert, L., Cazlaris, H., Georgopoulos, S., Kaslaris, E., Kioussis, D. & Kollias, G. (1991) *Embo J* 10, 4025-31). Mice were monitored for evidence of arthritis in the four paws using a blinded procedure. For each limb, clinical severity was scored from 0 (normal) to 3 (severe inflammation with deformation (Williams, R. O., Feldmann, M. & Maini, R. N. (1992) *Proc Natl Acad Sci USA* 89, 9784-8; Thwin, M. M., Douni, E., Aidinis, V., Kollias, G., Kodama, K., Sato, K., Satish, R. L., Mahendran, R. & Gopalakrishnakone, P. (2004) *Arthritis Res Ther* 6, R282-94). The mean arthritis score on each clinical observation day was calculated in each treatment group. For histological analysis, the legs were dissected free and processed as described elsewhere (Bessis, N., Guery, L., Mantovani, A., Vecchi, A., Sims, J. E., Fradelizi, D. & Boissier, M. C. (2000) *Eur J Immunol* 30, 867-75). Extensive sections were cut for each paw and at least four were examined. The lesions were blindly evaluated for each joint in knee, ankle and foot, as previously described using a four-point scale (0-3, where 0 is normal and 3 severe) either for synovitis (synovial proliferation, inflammatory cell infiltration) or joint destruction (bone and cartilage thickness and irregularity and presence of erosions) (Saidenberg-Kermanac'h, N., Corrado, A., Lemeiter, D., deVernejoul, M. C., Boissier, M. C. & Cohen-Solal, M. E. (2004) *Bone* 35, 1200-7, Miellot, A., Zhu, R., Diem, S., Boissier, M. C., Herbelin, A. & Bessis, N. (2005) *Eur J Immunol* 35, 3704-13).

A.14. Statistical analysis. All statistics were done using the StatView version 5.0 Software. ANOVA was used to analyse repeated measures such as clinical scores, number of affected limbs, weight gain, prevalence. For comparison of quantitative data, the non parametric Mann Whitney test was used. Chi-square with Yates correction was used to compare qualitative data.

B. Results of Examples 8 to 12

Example 8

Biological Properties of the Stable Immunogenic Product (hTNFα Kinoid)

A. Immuno-Biochemical Characterization

Figure 8:
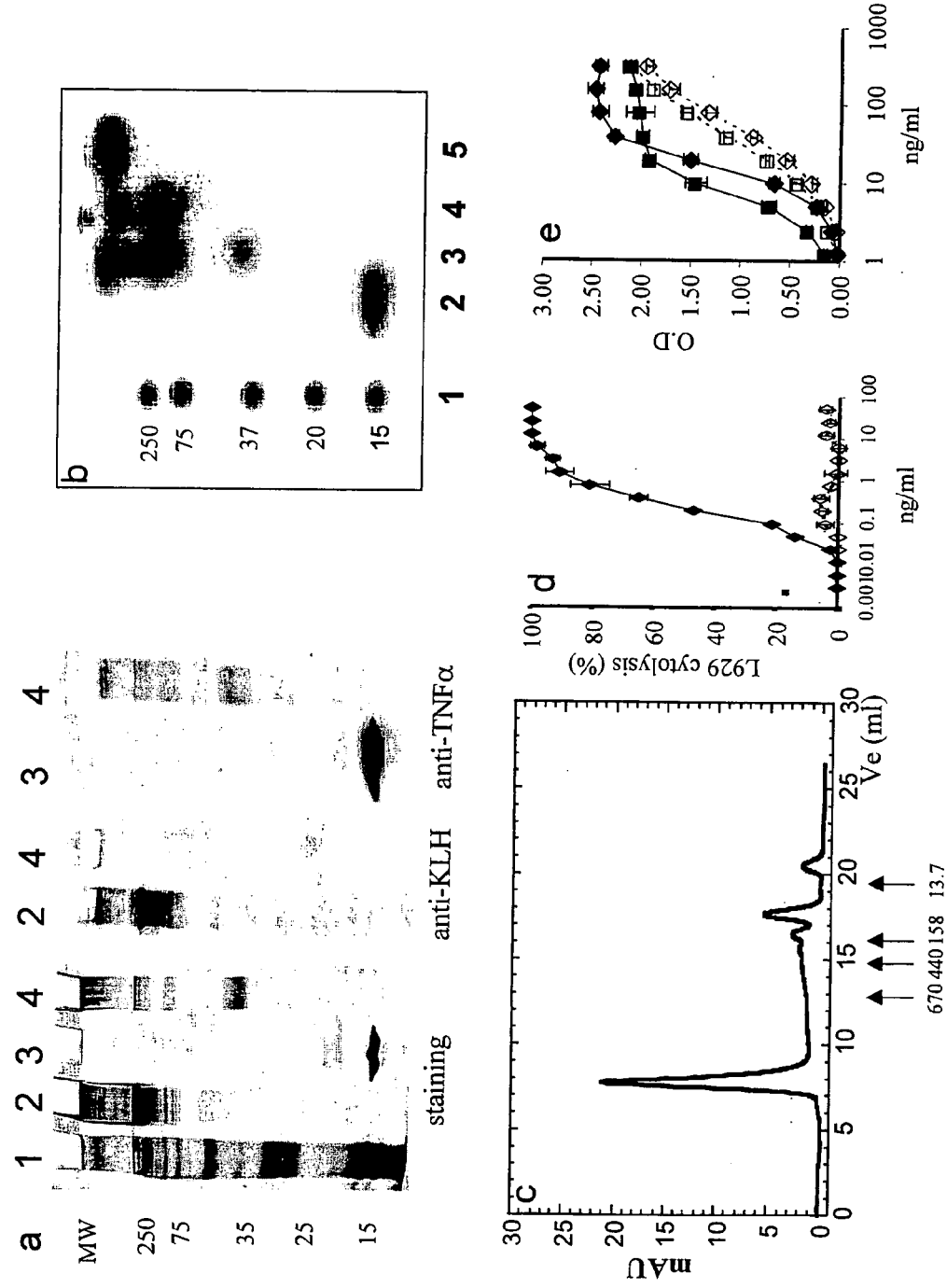

Human TNFα kinoid is a KLH-hTNFα heterocomplex that migrated in SDS-PAGE as 3 bands exhibiting molecular weights (MW) of about 250, 105 and 40 kDa (FIG. 8-*a*). A rather large proportion of the kinoid did not migrate and is visualized at the level of the stacking gel. Both hTNFα and KLH were identified with specific antibodies (FIG. 8-*a*).

A similar diagram of migration was obtained with $^{125}$I-labelled kinoid at either KLH or hTNFα as shown in FIG. 8-*b*. Four peaks were resolved on superose 6 gel filtration. One peak was in the exclusion volume while the 3 others were of MWs 440, 158 and 13.7 kDa (FIG. 8-*c*).

B. Absence of TNFα Bioactivity

The kinoid was devoid of any TNFα-induced cytotoxicity as assessed by standard L929 test even at the highest concentrations (FIG. 8-*d*).

Human TNFα-kinoid bound to both the hTNFα receptor I (p55) and receptor II (p75) despite its desirable lack of bioactivity (FIG. 8-*e*).

Example 9

Induction of Anti-TNFα Antibodies in Mice Transgenic for Human TNFα (TTq Mice)

Figure 9:
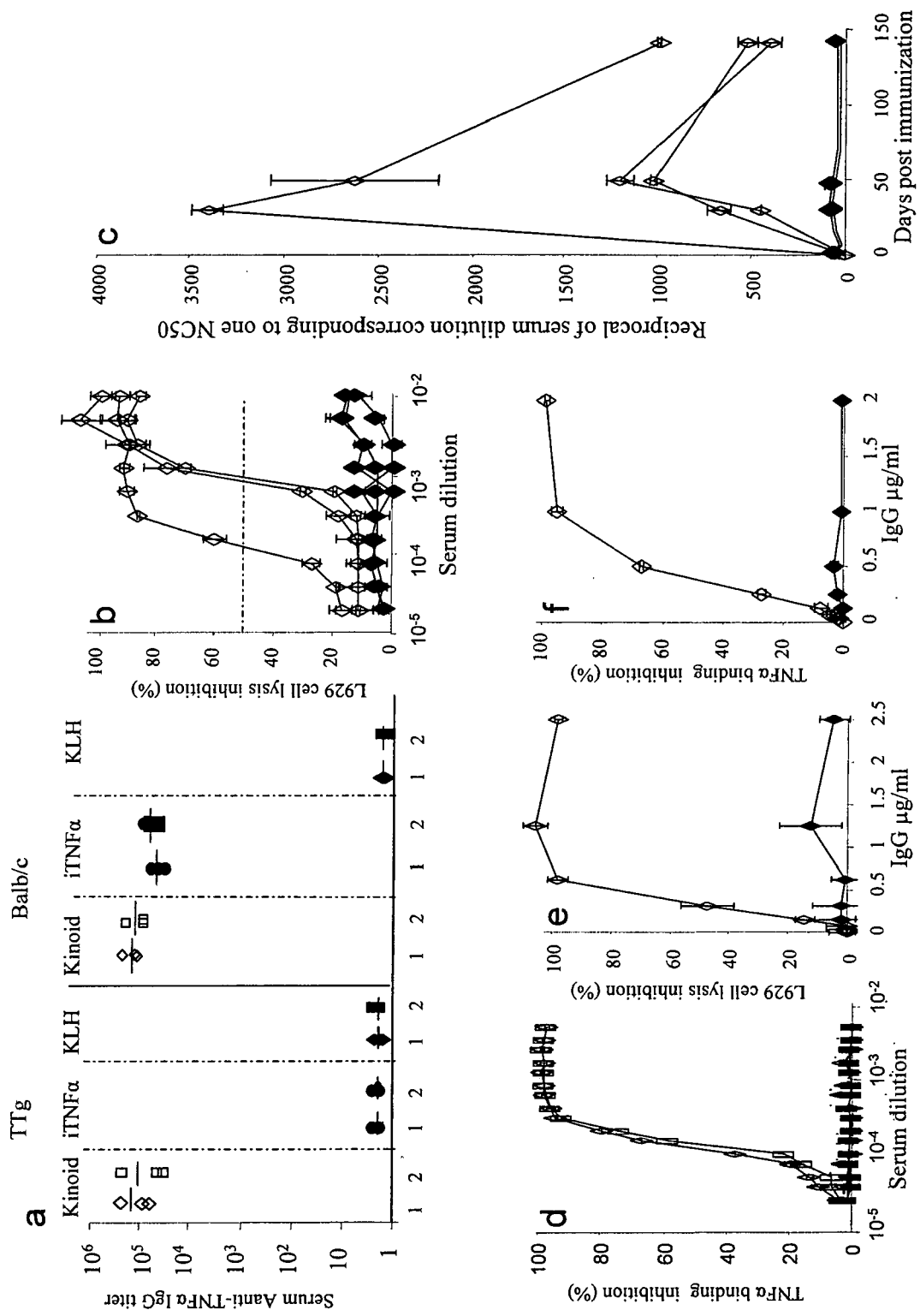

In TTg mice immunization with TNFα kinoid induced high titers of anti-TNFα Abs, whereas immunization with inactivated TNFα or with control KLH failed to elicit any detectable anti-TNFα Abs. By contrast in Balb/c mice both immunization with kinoid or with inactivated TNFα elicited anti-TNFα Abs (FIG. 9-*a*). In TTg and BalbC mice, KLH but also kinoid immunizations resulted in generation of anti-KLH Abs (not shown). As assessed by standard L929 cytotoxicity tests, hyperimmune sera at high dilution from kinoid immunized TTg mice, neutralized TNFα bioactivity even at high dilution, whereas there was no effect of sera from KLH immunized mice (FIG. 9-*b*). The activity peaked 2-4 weeks post boosting, declined markedly (>50%) within 3 months (FIG. 9-*c*) and blocked the binding of TNFα R1 and R2 receptors (FIG. 9-*d*). Anti-hTNFα Abs belonged mainly to IgG1 (52%) and IgG2a (48%). There were negligible amounts of IgG3, IgM and IgE, as measured by isotyping Elisa kits. Finally purified IgG from hyperimmune sera exhibit high affinity for huTNFα withKD ranging from $5\times10^{-8}$ M to $10^{-10}$ M as assessed by Biacore technology and blocked the binding of hTNFα to its receptors I and II (FIG. 9-*f*). These results explain why circulating hTNFα was not detected in sera of immunized mice in contrast to its presence in unimmunized mice at 9 pg/ml.

Example 10

Safety of the Stable Immunogenic Product (hTNFα Kinoid)

Administration of high doses of TNFα kinoid (up to 100 µg) did not generate regional or systemic clinical side effects in different strains of mice (Balb/c; C57BI/6; Swiss), rabbits or monkeys (*Maccaca mulata*). Also, whereas native hTNFα administered in D-galactosamine-treated C57BI/6 mice caused death within 24 hours (8 of 8 mice) there was no effect of the hTNFα kinoid. Furthermore kinoid immunization did not elicit adverse effects including undesirable anti-hTNFα cellular autoimmune response and impairment of long term growth and survival of immunized TTg mice.

Figure 10:
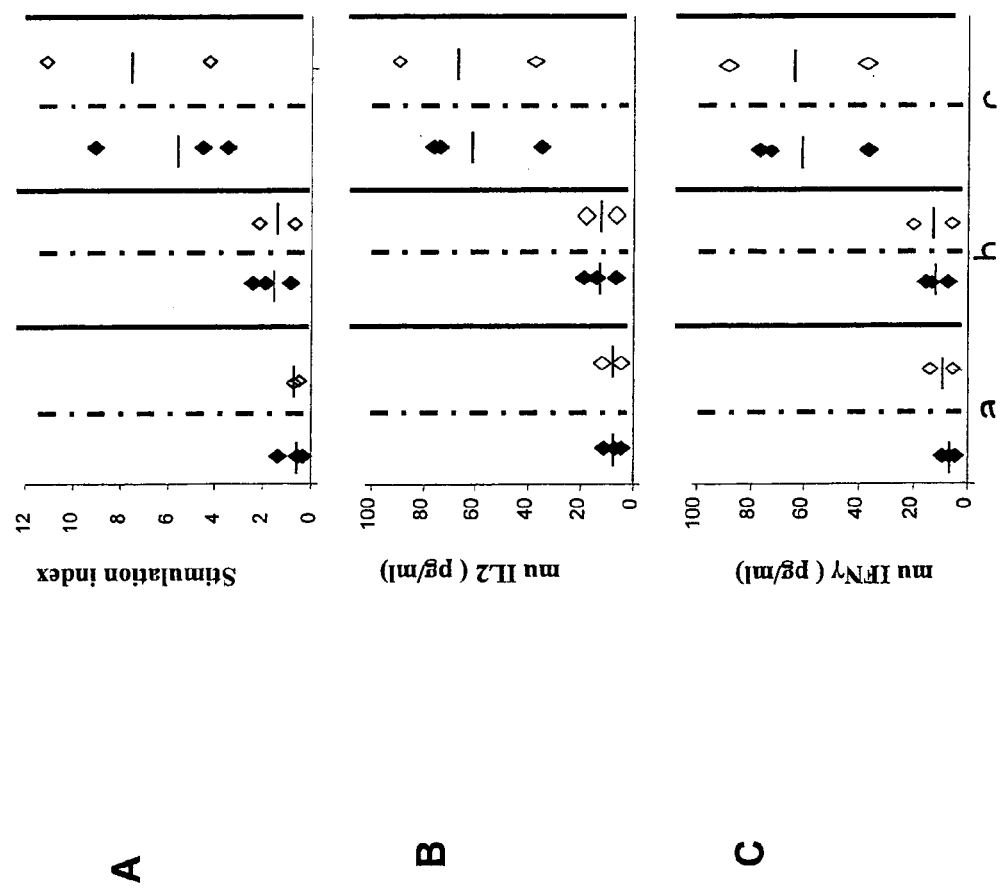

In vitro culture of splenocytes from kinoid immunized TTg mice did not trigger any cell mediated immune response to self hTNFα, as tested by T-cell proliferation and by cytokine (Il-2 and IFNγ) production in culture supernatants (FIG. 10(A, B, C)-a). By contrast kinoid immunized Balb/c mice exhibited notable cell mediated immunity to heterologous hTNFα compared to control non immunized animals (not shown). No cellular response to muTNFα could be detected in immunized mice compared to controls (FIG. 10(A, B, C)-b). Finally, in immunized TTg mice a comparable positive T cell response to KLH antigen, equal to that of control animals receiving KLH was observed which had no detectable clinical effects (FIG. 10(A, B, C)-c).

Growth of kinoid immunized mice (n=8), as measured by body weight, was comparable to that of control non immunized animals (n=7) up to 50 days post-immunization but became significantly better in later stages (FIG. 11-*a*). The mice were sacrificed at day 120 post-immunization for a comparative histological study of joint tissues. Other groups of TTg mice were followed longer in order to observe clinical progression of their arthritis. Among these animals, controls (n=3) were sacrificed at day 150 because of the severity of their arthritis. In contrast the 3 hTNFα-kinoid immunized TTg mice have remained free from severe arthritis (now over 210 days).

Example 11

Prevention of TNFα-Galactosamine Lethal Shock by Neutralizing Antibodies Induced by Vaccination with a Stable Immunogenic Product (hTNFα Kinoid)

Intraperitoneal administration of TNFα may trigger in presence of galactosamine a lethal shock in mice. The effect is dose-dependent. As shown in Table 1 in C57BI/6 mice the lethal shock occurred at a dose of 11 µg, and in TTg mice death was recorded at a dose as low as 1 µg.

All non-vaccinated control but none of the hTNFα-kinoid immunized C57BI/6 mice treated with 11 µg hTNFα died (Table 6). It is worth noting that the immunized animals not only withstood lethal shock, they also remained clinically healthy. Moreover a repeated hTNFα-galactosamine administration at one month intervals had no effects (not shown).

Importantly, kinoid immunized TTg mice, also resisted hTNFα dependent lethal shock, whereas control TTg mice died (Table 6). Administration of higher dosages of hTNFα (2 µg) had no effect on hTNFα kinoid immunized TTg mice (Table 6). These animals survived following a repeated hTNFα shock after 2 weeks and remained fully healthy up to now.

In immunized mice protection against the shock was due to neutralizing anti-TNFα Abs. Whereas control C57Bl/6 mice receiving non-specific IgG (1 mg) one hour following TNFα (11 μg)-D-galactosamine administration died within 24 hours, mice given specific purified polyclonal IgG from hyperimmune sera survived (P<0.001 vs control group). In these experiments an additional subgroup of control and immunized mice were sacrificed 8 h post hTNFα administration, and macroscopic organ analysis showed liver atrophy in control but not in immunized mice (P<0.02 vs control) (Table 7).

Example 12

Vaccination with a Stable Immunogenic Product (hTNFα Kinoid) Protects TTg Mice from Development of Arthritis Seven week old TTg mice were vaccinated with KLH/TNF-α kinoid and monitored during a 120 day period. Control groups consisted of KLH-treated and saline-treated mice, and neither affected the arthritis. All control mice developed polyarthritis with inflammation and joint deformations (FIG. 11), whereas kinoid vaccinated mice had only marginal articular disease (P<0.0001) (FIG. 4-c), with a delay on onset of clinical signs (P.<0.05), a low score of maximal clinical index (p<0.01) (Table 8)) and a grossly less diffuse disease and far less affected limbs (P<0.0001) (FIG. 11-b). Although all animals developed clinical arthritis, the disease reversed only in the TNF-α kinoid immunized group (FIG. 11-d); at day 120, all animals except one were protected in the treated group (Table 8), in contrast to the control group (P.<0.001).

Histological evaluation showed a frank reduction of inflammation and joint destruction in treated animals that exhibited low histological scores (P.<0.01) (Table 8); by contrast, control mice showed significant evidence of arthritis, with proliferative synovitis and cell infiltrate with mononuclear and polymorphonuclear cells, associated with cartilage and bone erosions. The incidence of histological synovitis or destruction were significantly reduced in TNFα-kinoid treated mice (Table 8).

TABLE 6

TNFα-dependent lethal shock:
hTNFα in presence of D-galactosamine was administered by IP in 0.1 ml PBS 10 days after the last boost to control and kinoid immunized C57Bl/6 and TTg mice.
Prevention of lethal shock as evaluated by animal survival after 24 hours was observed only in immunized mice.

| | | Mice Survival at 24 hours (alive/total) | | | |
|---|---|---|---|---|---|
| | hTNFα | C57Bl/6 | | TTg | |
| | (μg/mouse) | Control | Immunized | Control | Immunized |
| Experiment 1 | 1 | 6/6 | 6/6 | 0/6 | 6/6* |
| Experiment 2 | 11 | 0/6 | 6/6 | Not done | Not done |
| Experiment 2 | 2 | 6/6 | 6/6 | Not done | 6/6 |
| Experiment 2 | 1 | 6/6 | 6/6 | 0/6 | 6/6* |

*P < 0.01 vs control (chi-2)

TABLE 7

Neutralization of TNFα-dependent shock by hyperimmune IgG
Groups of mice received D-galactosamine and hTNFα by IP in 0.1 ml PBS 30 min before the IV injection of protein G-purified mouse IgG from control and kinoid immunized C57Bl/6 mice.

| | hTNFα (μg/mouse) | Mice Survival at 24 hours (alive/total) | Liver atrophy |
|---|---|---|---|
| Control mice | 11 | 0/10 | 5/5 |
| TNF-kinoid immunized mice | 11 | 10/10* | 0/5† |

*P < 0.001 vs control (chi-2).
†P < 0.02 (chi-2)

TABLE 8

Clinical and histological scores of arthritis in TNF-α kinoid (KLH-TNF) vaccinated and in control (KLH) mice at day 120.
Incidence of inflammation/destruction as evaluated by histology is the number of mice with a score of inflammation/destruction ≧0.5. Amax: maximum arthritis clinical score.

| | | Clinical evaluation | | | Histology | | | |
|---|---|---|---|---|---|---|---|---|
| | | Arthritis | | | Inflammation | | Destruction | |
| Immunization | Animal | Onset (days) | Amax Score | Prevalence | Score | Prevalence | Score | Prevalence |
| KLH | 7 | 36.1 ± 4.5 | 8.6 ± 0.6 | 7 | 1.5 ± 0.1 | 7 | 1.2 ± 0.1 | 7 |
| KLH-TNF | 8 | 49.5 ± 3.2* | 1.4 ± 0.2† | 1‡ | 0.1 ± 0.1† | 0‡ | 0.1 ± 0.1† | 1‡ |

Results are given as mean ± SEM.
*p < 0.05 vs KLH,
†p < 0.01 vs KLH (Mann Whitney);
‡p < 0.001 vs KLH (Chi 2)

The invention claimed is:

1. A method for preparing a stable anti-TNFα immunogenic product for human immunization consisting of heterocomplexes of TNFα and keyhole limpet haemocyanin (KLH) and having an ED50 value of more than 400 ng/ml according to an L929 cell cytotoxicity assay, the method comprising the steps of:
   a) providing a liquid solution containing TNFα at a concentration ranging from 0.1 mg/ml to 50 mg/ml;
   b) adding EDTA and DMSO to said liquid solution containing TNFα of step a) to provide a final concentration of EDTA ranging from 1 mM to 500 mM and a final amount of DMSO ranging from 0.5% v/v to 20% v/v;
   c) adding a KLH carrier protein to the liquid solution obtained at the end of step b) to provide a molar ratio of TNFα to KLH ranging from 20:1 to 80:1;
   d) adding glutaraldehyde to the liquid mixture obtained at the end of step c) to obtain a final glutaraldehyde concentration ranging from 0.05% w/w to 0.5% w/w;
   e) removing glutaraldehyde and free molecules of both TNFα and KLH from the solution obtained at the end of step d);
   f) adding formaldehyde to the liquid solution obtained at the end of step e) and maintaining the presence of formaldehyde for a period of time ranging from 96 hours to 192 hours;
   g) adding a reagent comprising at least one amino group that blocks the reaction with formaldehyde to the liquid solution obtained at the end of step f); and
   h) removing formaldehyde and the blocking reagent from the liquid solution obtained at the end of step g), so as to obtain a liquid solution containing said anti-TNFα immunogenic product, the product having an ED50 value of more than 400 ng/ml according to an L929 cell cytotoxicity assay.

2. The method according to claim 1, wherein step d) comprises the following steps:
   d1) adding glutaraldehyde to the liquid mixture obtained at the end of step c); and
   d2) adding EDTA to the heterocomplexes between TNFα and said carrier protein obtained at the end of step d1).

3. The method according to claim 1, wherein at step a) TNFα concentration ranges from 0.5 mg/mL to 10 mg/mL.

4. The method according to claim 2, wherein at step d2) final EDTA concentration ranges from 1 mM to 10 mM.

5. The method according to claim 1, wherein at step e) glutaraldehyde is removed by performing a dialysis, by performing an ultrafiltration with diafiltration or by performing Tangential Flow Filtration (TFF).

6. The method according to claim 1, wherein at step f), the final concentration of formaldehyde ranges from 0.1% w/w to 1% w/w.

7. The method according to claim 1, wherein at step f), the final concentration of formaldehyde ranges from 0.2% w/w to 0.5% w/w.

8. The method according to claim 1, wherein at step f) the presence of formaldehyde is maintained during a period of time ranging from 120 hours to 168 hours.

9. The method according to claim 1, wherein at step g), the blocking reagent consists of glycine.

10. The method according to claim 9, wherein at step g) final glycine concentration ranges from 0.01 M to 10 M.

11. The method according to claim 9, wherein at step g) final glycine concentration ranges from 0.05 M to 2 M.

12. The method according to claim 1, wherein at step g), the blocking reagent consists of lysine.

13. The method according to claim 12, wherein at step g) final lysine concentration ranges from 0.01 M to 10 M.

14. The method according to claim 12, wherein at step g), final lysine concentration ranges from 0.05 M. to 0.5 M.

15. The method according to claim 1, wherein at step h) formaldehyde and the blocking reagent are removed by performing a dialysis, by performing an ultrafiltration with diafiltration or by performing Tangential Flow Filtration (TFF).

16. A method for preparing a vaccine composition comprising the steps of:
   a) preparing an anti-TNFα immunogenic product by performing the method of claim 1; and
   b) combining said anti-TNFα immunogenic product prepared at step a) with one or more immunoadjuvants.

* * * * *